US011284921B2

(12) United States Patent
Sun et al.

(10) Patent No.: US 11,284,921 B2
(45) Date of Patent: Mar. 29, 2022

(54) FRACTURE REDUCTION METHOD AND PARALLEL EXTERNAL FIXATOR FOR FRACTURE REDUCTION

(71) Applicant: BEIJING NATON MEDICAL TECHNOLOGY HOLDINGS CO., LTD., Beijing (CN)

(72) Inventors: Tao Sun, Tianjin (CN); Sida Liu, Tianjin (CN); Yimin Song, Tianjin (CN); Wei Yan, Tianjin (CN)

(73) Assignee: BEIJING NATON MEDICAL TECHNOLOGY HOLDINGS CO., LTD., Beijing (CN)

( * ) Notice: Subject to any disclaimer, the term of this patent is extended or adjusted under 35 U.S.C. 154(b) by 0 days.

(21) Appl. No.: 16/762,813

(22) PCT Filed: Aug. 28, 2018

(86) PCT No.: PCT/CN2018/102719
§ 371 (c)(1),
(2) Date: May 8, 2020

(87) PCT Pub. No.: WO2019/232939
PCT Pub. Date: Dec. 12, 2019

(65) Prior Publication Data
US 2021/0212729 A1    Jul. 15, 2021

(30) Foreign Application Priority Data

Jun. 5, 2018   (CN) .......................... 201810567844.2

(51) Int. Cl.
*A61B 17/64*    (2006.01)
(52) U.S. Cl.
CPC ...... *A61B 17/6441* (2013.01); *A61B 17/6475* (2013.01)

(58) Field of Classification Search
CPC .............................................. A61B 17/60–666
See application file for complete search history.

(56) References Cited

U.S. PATENT DOCUMENTS 4,308,863 A * 1/1982 Fischer .................. A61B 17/62
606/56
5,728,095 A   3/1998 Taylor et al.
(Continued)

FOREIGN PATENT DOCUMENTS

CN         202365897 U      8/2012
CN         102871714 A      1/2013
(Continued)

OTHER PUBLICATIONS

International Search Report of PCT/CN2018/102719.
Written Opinion of PCT/CN2018/102719.

*Primary Examiner* — Eduardo C Robert
*Assistant Examiner* — Steven J Cotroneo
(74) *Attorney, Agent, or Firm* — Hodgson Russ LLP

(57) ABSTRACT

A fracture reduction method and a parallel external fixator for fracture reduction for realizing the method, the fracture reduction method being used for existing six-chain ring-shaped parallel external fixators in minimally invasive fracture reduction or osteotomy of limbs. The parallel external fixator comprises two fixation rings, six struts and six markers, the fixation rings are arranged with a plurality of connecting holes, the struts are arranged with a spherical hinge, a driving joint (1302), a quick-mounting component and a universal hinge, the markers comprise marker balls and a pin shaft. The parallel external fixator can improve the treatment accuracy, reliability and operation convenience.

4 Claims, 18 Drawing Sheets

(56) References Cited

U.S. PATENT DOCUMENTS

| | | | | |
|---|---|---|---|---|
| 6,030,386 | A * | 2/2000 | Taylor | A61B 17/62 606/54 |
| 8,439,914 | B2 | 5/2013 | Ross et al. | |
| 8,444,644 | B2 * | 5/2013 | Ross | A61B 17/62 606/56 |
| 8,454,604 | B2 | 6/2013 | Wong | |
| 8,906,021 | B1 * | 12/2014 | Lehmann | A61B 17/66 606/57 |
| 9,524,581 | B2 | 12/2016 | Haskell | |
| 9,717,530 | B1 * | 8/2017 | Ross | A61B 17/6491 |
| 10,751,089 | B2 * | 8/2020 | Wigginton | A61B 17/66 |
| 10,856,908 | B2 * | 12/2020 | Mullaney | A61B 17/6475 |
| 2003/0191466 | A1 * | 10/2003 | Austin | A61B 17/62 606/54 |
| 2004/0068187 | A1 * | 4/2004 | Krause | A61B 17/15 600/443 |
| 2007/0055234 | A1 * | 3/2007 | McGrath | A61B 17/62 606/56 |
| 2011/0208187 | A1 * | 8/2011 | Wong | A61B 17/6416 606/59 |
| 2012/0041439 | A1 * | 2/2012 | Singh | A61B 17/60 606/54 |
| 2013/0041288 | A1 * | 2/2013 | Taylor | A61B 5/4884 600/587 |
| 2013/0204248 | A1 * | 8/2013 | Singh | A61H 3/00 606/56 |
| 2016/0022314 | A1 * | 1/2016 | Bordeaux | A61B 17/60 606/56 |
| 2016/0066956 | A1 * | 3/2016 | Siemer | A61B 17/62 606/56 |
| 2017/0354439 | A1 * | 12/2017 | Mannanal | A61B 17/66 |
| 2018/0214181 | A1 * | 8/2018 | Mannanal | A61B 17/62 |
| 2021/0000508 | A1 * | 1/2021 | Sun | A61B 90/39 |

FOREIGN PATENT DOCUMENTS

| | | |
|---|---|---|
| CN | 105050517 A | 11/2015 |
| EP | 2767252 A1 | 8/2014 |
| WO | 2009102904 A1 | 8/2009 |
| WO | 2011163406 A2 | 12/2011 |
| WO | 2019232939 A1 | 12/2019 |

* cited by examiner

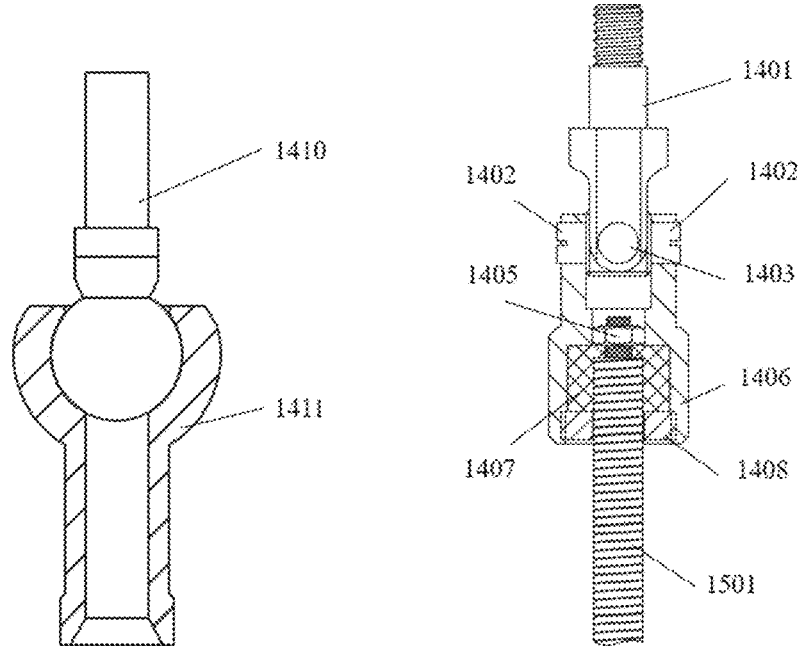
FIG. 14 A
FIG. 14 B
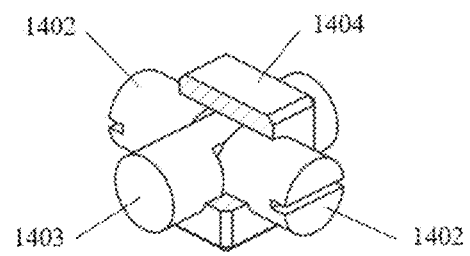
FIG. 14C
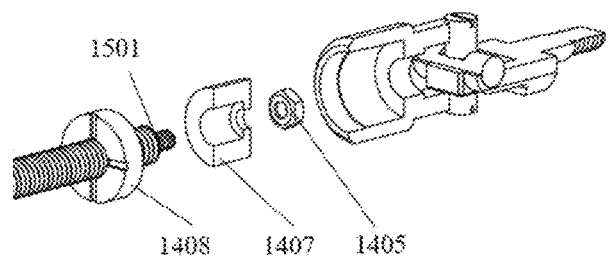
FIG. 14D

FRACTURE REDUCTION METHOD AND PARALLEL EXTERNAL FIXATOR FOR FRACTURE REDUCTION

CROSS-REFERENCE TO RELATED APPLICATIONS

This application is a national stage application of PCT Application No. PCT/CN2018/102719. This application claims priority from PCT Application No. PCT/CN2018/102719, filed Aug. 28, 2018, CN Application No. CN 201810567844.2 filed Jun. 5, 2018, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

FIELD OF THE INVENTION

The present invention relates to the field of orthopedic external fixation, in particular to a method for guiding fracture reduction based on three-dimensional images, and a parallel external fixator with struts which can be freely configured and can be quickly assembled and disassembled on the whole.

BACKGROUND OF THE INVENTION

Fracture is a common symptom in orthopedics. Fractured bone segments need to be fixed by certain means after reduction treatment. At present, fracture fixation methods commonly used include plaster, splints, intramedullary nails, external fixators. Compared with other fixing methods, external fixators have advantages such as minimal invasion and extensive adaptability. External fixators can be divided into unilateral external fixators and parallel external fixators. Compared with unilateral external fixators, parallel external fixators have better stability and can be accurately adjusted to realize fine adjustment for fracture reduction. In addition, parallel external fixators can also be used for limb orthopedic treatment to rebuild the shape of osteotomy cut bone segments during a long period of time.

U.S. Pat. Nos. 6,030,386A, 8,439,914B2 and WO2011163406A2 provide a kind of parallel external fixators, wherein such fixators consist of six struts with the same topological structure and two fixation rings. Struts are arranged in a circularly symmetric manner and respectively connected with the two fixation rings through hinges at both ends. The two fixation rings are fixedly connected with each of the two fractured bone segments of a patient by using metal bone pins and are connected with the six struts to achieve fracture fixation. Also, adjusting the lengths of the six struts according to a certain method can make the two fixation rings in combination with the fractured bone segments to generate relative movement in space, which can achieve fine adjustment for fracture reduction. The parallel external fixators provided by the above patents has the following defects: 1) the connection between the six struts and the fixation rings is only in a circularly symmetric manner, and interference between the struts and the bone pins occurs occasionally during clinical mounting; 2) the scale resolution of the driving joint in the strut is not high, and the strut adjustment accuracy is low; 3) the driving joint of the strut cannot be locked in the fracture fixation state, and the gap leads to the decrease of the stability of the fixator.

The struts of the parallel external fixator are in a parallel topological structure. Therefore, the movement for fracture reduction is produced by the adjustment movement coupling of all driving joints. A method for solving the length adjustment solution for the six struts is required. The methods provided by U.S. Pat. Nos. 9,524,581, 5,728,095 and EP2767252 can be realized through the following processes: firstly taking X-ray frontal and lateral films of a fracture position with the entire external fixator; secondly manually measuring the position and pose parameters between fracture ends on the X-ray images and the mounting parameters between the bone segment and the external fixator, and reading the length of each strut of the external fixator; then inputting the information into the computer system, and solving the adjustment solution for all driving joints of the struts by using a certain algorithm to form an electronic prescription, and finally adjusting the length of the six struts of the external fixator according to the electronic prescription to achieve the fracture reduction. The reduction methods provided by the above patents have the following defects: 1) the X-ray frontal and lateral films cannot reflect the rotation deformity around the diaphysis axis of the fracture site, and factors such as the X-ray image shooting angle, shooting distance, and the patient's limb placement cannot be standardized; 2) there are many subjective and objective errors in manual measurement of X-ray images; 3) such methods fail to visualize fracture reduction movement, making it difficult to predict the possible interference between the bone segments during fracture reduction.

Therefore, a heretofore unaddressed need exists in the art to address the aforementioned deficiencies and inadequacies.

SUMMARY OF THE INVENTION

The purpose of the present invention is to overcome the drawbacks of the prior art, to provide a deformity correction method suitable for the existing six-chain ring-shaped parallel external fixators in minimally invasive fracture reduction or osteotomy of limbs, and provide a parallel external fixator which can better realize the method provided by the present invention.

Terms and Definitions

The following definitions are provided to define the used terms more clearly. Unless otherwise indicated, the following definitions apply to this disclosure. To the extent that any definition or usage provided by any document incorporated herein by reference conflicts with the definition or usage provided herein, the definition or usage provided herein controls.

The term "connection" used herein refers to a mechanical connection, and two components constitute one unit body having a relative movement or a relatively fixed structure through a certain mechanical structure.

The term "fixed connection" used herein refers to three kinds of connections, which are, the bone and fixation ring connection, the marker and fixation ring connection, and quick-mounting components connection; wherein, the bone and fixation ring connection a general fracture fixation method in the technical field of orthopedic surgery fixation technology, that is, using metal bone pins to pass through the fractured bone in the clinic, and using a fastener to fix the metal bone pins on the fixation rings so as to fix the fractured bones and the fixation rings relatively.

The term "proximal" and "distal" used herein refer to clinical terms, which use the heart as a reference to distinguish the two fractured bone segments and the corresponding fixation rings.

The term "position" and "pose" are commonly used in the technical field of robotics to describe the rigid body state, where "position" defines three translational degrees of freedom of the rigid body, and "pose" defines three rotational degrees of freedom of the rigid body.

The term "three-dimensional reconstruction" used herein refers to a technical means in the field of medical imaging, which obtains a three-dimensional image with a single/multiple entities through a set of plane perspective images so that the actual spatial state of fractured bones and fixation devices can be obtained.

The term "sphere fitting algorithm" used herein refers to an algorithm of computer graphics, which calculates the center position of the sphere by using a set of data points distributed on the sphere. An exemplary sphere fitting algorithm in the present invention includes but is not limited to: selecting point cloud of a spherical three-dimensional image of a certain marker, extracting the coordinates of each point and fitting the spherical equation by using the least square method to obtain the coordinates of the spherical center of the spherical equation, and identifying the center position of the three-dimensional sphere.

The term "adjustment solution" used herein refers to a struts length adjustment solution for users, which adjusts struts according to the specified adjustment solution so as to achieve guiding fracture reduction/correction of fracture deformities.

The term "matrix" used herein refers to a means of recording a set of related data. In the embodiment of the present invention, the matrix can be, but is not limited to: a *.xls file recorded using a software of Microsoft Excel, or a *.mat file recorded using Math Works MATLAB.

The terms "fracture reduction" and "limb deformity correction" used herein refer to treatment modes according to two clinical treatment of fracture and limb deformation; normally, "fracture reduction" reduces the bone fracture and builds natural bone shape directly, while "limb deformity correction" reduces the limb deformity progressively over a long period of time, while the deformed bone builds natural shape gradually.

The present invention is implemented by adopting the following technical solution.

A fracture reduction method comprises the following steps:

(1) mounting an external fixator according to the following steps:

(a) for a patient with a fracture or limb deformity, after clinical trauma treatment or deformed bone osteotomy, fixedly connecting a proximal bone segment and a distal bone segment at the fracture position respectively with a proximal fixation ring and a distal fixation ring of an external fixator;

(b) connecting a first strut, a second strut, a third strut, a fourth strut and a sixth strut between the proximal fixation ring and the distal fixation ring; and (c) selecting three connecting holes which are not connected with any parts and are distantly separate from each other in the proximal fixation ring, and respectively inserting a first marker, a second marker and a third marker to form a fixed connection; and selecting three connecting holes which are not used and are distantly separate from each other in the distal fixation ring, and respectively inserting a fourth marker, a fifth marker and a sixth marker to form a fixed connection between the distal fixation ring and each marker, wherein the six markers have the same structure and respectively comprise a marker ball with an internal threaded hole, and a marker pin shaft in threaded connection with the marker ball, the marker pin shaft is capable of being directly inserted into the connecting hole of the fixation ring to realize fixed connection, the marker ball is made of a metal material, and the marker pin shaft is made of a plastic material;

(2) recognizing position and pose information according to the following steps:

(a) scanning the fracture position and the entire external fixator by using an existing three-dimensional medical CT imaging device, performing image processing and three-dimensional reconstruction such that the six marker balls are recognized to form a first three-dimensional sphere, a second three-dimensional sphere a third three-dimensional sphere, a fourth three-dimensional sphere, a fifth three-dimensional sphere and a sixth three-dimensional sphere to obtain a three-dimensional image including a proximal bone segment three-dimensional solid, a distal bone segment three-dimensional solid, and six three-dimensional spheres, and storing the three-dimensional image in a computer system;

(b) specifying a corresponding relationship between the first three-dimensional sphere to the sixth three-dimensional sphere and the first marker to the sixth marker on the external fixator in the three-dimensional image by using a computer operating interface;

(c) recognizing, by the computer system, the center positions of the first three-dimensional sphere to the sixth three-dimensional sphere in the three-dimensional image by using a sphere fitting algorithm, and determining the position and pose of the proximal fixation ring in the three-dimensional image by using the center positions of the first three-dimensional sphere, the second three-dimensional sphere and the third three-dimensional sphere; and determining the position and pose of the distal fixation ring in the three-dimensional image by using the center positions of the fourth three-dimensional sphere, the fifth three-dimensional sphere and the sixth three-dimensional sphere; and (d) solving and recording, by the computer, the relative spatial position and pose information of the proximal fixation ring and the distal fixation ring in the initial mounting condition by using a kinematic algorithm in the robotic field, and removing the first marker to the sixth marker after the recognition of the position and pose information;

(3) planning fracture reduction or limb deformity correction movement according to the following steps:

(a) observing the proximal bone segment three-dimensional solid and the distal bone segment three-dimensional solid in the computer operating interface, and adjusting the relative spatial states of the proximal bone segment three-dimensional solid and the distal bone segment three-dimensional solid by using input devices such as a keyboard and a mouse according to expected fracture reduction or limb deformity correction movement, so as to form fracture reduction or limb deformity correction movement steps;

(b) sequentially recording, by the computer system, the relative position and pose information of the proximal fixation ring and the distal fixation ring in each movement step, so as to determine the relative spatial state of the proximal bone segment and the distal bone segment, the computer calculating the variation value of the relative position and pose information of the proximal fixation ring and the distal fixation ring between current movement step and the previous movement step, and automatically performing interpolation to obtain a discrete movement trajectory of fracture reduction or limb deformity correction; and (c) drawing, by the computer system, the animation simulation of the relative movement of the proximal bone segment three-dimensional solid and the distal bone segment three-dimensional solid of the fracture in the operating interface based on the discrete movement trajectory, the operator checking whether the animation simulation meets the expected movement and whether there is a collision between the fractured bone segments; if the simulation result is unsatisfactory, returning to the beginning of step (a) of this step (3) to plan movement steps again; and if the simulation result is acceptable, the computer system storing the discrete movement trajectory of fracture reduction or limb deformity correction;

(4) performing solving to obtain an adjustment solution, wherein a solving method comprises the following steps: according to the stored discrete movement trajectory obtained in step (3), solving, by the computer system, the length data of the first strut to the sixth strut at each discrete point of the discrete movement trajectory by using a kinematic algorithm of parallel mechanisms in the robotic field, and storing the struts length data in a discrete points struts length matrix; and selecting a "fracture reduction" mode or a "limb deformity correction" mode in the computer operating interface according to the treatment type of a patient; in the "fracture reduction" mode, the computer reading the struts length data at each fracture reduction movement step from the discrete points struts length matrix, and arranging the struts length data according to the sequence of the movement steps to form an adjustment solution for fracture reduction; in the "limb deformity correction" mode, the operator setting the maximum daily displacement for limb deformity correction according to the distraction osteogenesis principle in the field of orthopedics; the computer selecting a plurality of discrete points from the limb deformity correction movement trajectory according to the sequence of the movement steps, and by respectively taking the set maximum daily displacement for limb deformity correction as the maximum interval to form daily limb deformity correction trajectory points; and selecting the struts length data from the discrete points struts length matrix according to the daily limb deformity correction trajectory points, and performing arrangement to form an adjustment solution for limb deformity correction; and (5) adjusting the external fixator, wherein a method comprises the following steps: according to the mode selected in step (4), for the "fracture reduction" mode, according to the adjustment solution for fracture reduction and the struts length data at each step in the adjustment solution, continuously adjusting the lengths of the six struts to reduce the fracture by the external fixator directly; for the "limb deformity correction" mode, according to the adjustment solution for limb deformity correction, adjusting the lengths of the six struts every day so as to gradually correct the limb deformity within a certain period of time by the external fixator.

A parallel external fixator for fracture reduction comprises:

a proximal fixation ring and a distal fixation ring provided below the proximal fixation ring, where the proximal fixation ring and the distal fixation ring having the same ring structure, six protrusions being uniformly provided at an interval on the sidewall of the ring structure, a plurality of inner ring connecting holes with axis in a vertical direction being uniformly provided at an interval in the entire ring structure, and outer ring connecting holes with axis in the vertical direction being uniformly provided at an interval in the six protrusions; six struts with the same structure being provided between the proximal fixation ring and the distal fixation ring, the six struts being freely configured according to the following rules that: the first strut to the sixth strut are sequentially provided around the circumferential direction of the fixation ring, and every two adjacent struts are not in parallel with each other and do not intersect with each other, the struts being characterized in that:

ach strut comprises a spherical hinge, a driving joint, a quick-mounting component and a universal hinge which are sequentially connected from top to bottom;

the driving joint is a screw mechanism, the lower screw section of the screw rod sequentially inserts into the middle threaded hole of a driving nut and the middle hole of a sliding sleeve, the screw rod and the driving nut form a screw movement pair, the driving nut comprises a cylindrical part, a boss with a diameter smaller than the diameter of the cylindrical part is provided on the top wall of the cylindrical part, the upper part of the sliding sleeve is inserted in the cylindrical part and is in rotary fit with the inner wall of the cavity of the cylindrical part, a plurality of steel ball holes with axis in the vertical direction are uniformly provided at an interval in the circumferential direction on the top wall of the cavity of the cylindrical part, a spring hole corresponding to steel ball hole is provided in the top surface of the sliding sleeve, a spring is mounted in the spring hole, the bottom end of the spring is connected with the bottom wall of the spring hole and a steel ball is fixed at the top end of the spring; the depth of the steel ball hole is smaller than the radius of the steel ball, and when rotating the driving nut, the steel ball is periodically and partially embedded into or withdrawn from the steel ball hole under the effect of the spring to provide a vibration tactile feedback of rotary movement amount; an external thread is provided on the outer wall of the sliding sleeve located at the bottom of the cylindrical part, a locking ring sleeves the cylindrical part of the driving nut, and the lower end of the locking ring and the external thread on the sliding sleeve form a threaded connection; a groove is provided in the inner wall of the cavity at the upper end of the locking ring and is embedded with a gasket, the gasket sleeves the boss of the driving nut and is in sliding contact with the top wall of the cylindrical part to limit the axial movement of the driving nut, the locking ring is capable of pressing the gasket or loosening the gasket by rotating the locking ring, forming a "locked" working state or an "adjustable" working state for the driving joint, an observation slot is provided along the axial direction of the sidewall of the sliding sleeve, and a telescoping scale mark is provided along the axial direction of the sliding sleeve on the sidewall corresponding to the observation slot; an axial scale mark is provided along the axial direction of the sliding sleeve at the top end of the observation slot, the lower section of the screw rod is provided with a pin shaft, and the pin shaft is inserted into the observation slot and is capable of sliding relative to the observation slot; the head face of the pin shaft is provided with a transverse scale mark, the transverse scale mark and the telescoping scale mark are provided matching to each other to indicate the elongation or shortening value of the strut length; a circumferential scale mark is provided on the outer wall of the boss of the driving nut, the circumferential scale mark and the axial scale mark are provided relative to each other to indicate the rotation value of the driving nut relative to the sliding sleeve;

the lower part of the sliding sleeve is connected with the upper part of a removable rod through the quick-mounting component, the upper part of the removable rod has a circle mark, the lower part of the removable rod is provided with an external thread, the external thread of the removable rod and the threaded hole in the upper part of one universal hinge form a threaded connection, and a threaded shaft at the lower part of the universal hinge inserts into one outer ring connecting hole or inner ring connecting hole in the distal fixation ring and is fixedly connected with the distal fixation ring through a nut;

the first marker, the second marker and the third marker are respectively connected into the three connecting holes which are not connected with any parts and are distantly separate from each other in the proximal fixation ring, and the fourth marker, the fifth marker and the sixth marker are respectively connected into the three connecting holes which are not used and are distantly separate from each other in the distal fixation ring; the six markers have the same structure, which respectively comprise a marker ball with an internal threaded hole and a marker pin shaft in threaded connection with the marker ball, the marker pin shaft is inserted into and fixedly connected with the connecting hole, the marker ball is made of a metal material, and the marker pin shaft is made of a plastic material.

The spherical hinge comprises a connecting shaft whose upper end is a threaded shaft, and the threaded shaft of the connecting shaft is capable of inserting into one outer ring connecting hole or one inner ring connecting hole in the proximal fixation ring and is fixedly connected with the proximal fixation ring through a nut; and the lower end of the connecting shaft is pivotally connected with the both ends of the long shaft of a cross-shaft component, the cross-shaft component is mounted at the upper part of a revolute connecting sleeve, the outer ends of the other two short shafts of the cross-shaft component are respectively and pivotally connected into the hole of the revolute connecting sleeve, a plain bearing is pivotally mounted in the cavity of the lower part of the revolute connecting sleeve, the inner ring of the plain bearing is in fixed connection with the upper section of a screw rod, where the top of the screw rod inserts into the plain bearing and is fixedly connected with an anti-loosening nut to prevent the threaded connection between the plain bearing and the screw rod from loosening; a back nut is connected with the internal thread at the bottom of the cavity of the revolute connecting sleeve through an external thread, the inner hole of the back nut and the outer surface of the screw rod have a certain clearance, enabling the screw rod and the back nut a relatively free rotation, and the back nut is capable of axially positioning the plain bearing.

The present invention has the following beneficial effects:

(1) The information in the fracture reduction method provided by the present invention is extracted from three-dimensional medical CT images and has 1:1 proportion to the real spatial size, which can fully and accurately provide the spatial information of the fracture segments and the external fixator.

(2) The fracture reduction method uses the image recognition algorithm to extract three-dimensional position information, thus effectively avoiding subjective and objective errors in manual measurement of X-ray frontal and lateral images.

(3) When planning fracture reduction movement, the motion of fracture reduction is displayed through three-dimensional visualized animation simulation, which makes it easy for the operator to master the process of fracture reduction by using the external fixator and effectively avoids the risk of fracture segments interference in the process of fracture reduction.

(4) The six struts of the external fixator provided by the present invention can be arranged freely, thus effectively avoiding interference between the struts and the metal bone pins during clinical mounting.

(5) The driving joint of the strut has a rotation amount indicating structure for the driving nut, which can accurately indicate the movement amount of the driving joint, and realize accurate adjustment and positioning.

(6) The driving joint of the strut of the external fixator has a locking structure, which can lock the length of the strut and eliminate the tiny gap of the driving joint, thus improving the stability of the external fixator in fracture fixation.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

FIG. 14A illustrates a structural schematic view of a commercially available part used in a spherical hinge of the strut; FIG. 14B, FIG. 14C and FIG. 14D respectively illustrate schematic views of a preferred the spherical hinge including an overall sectional structure, a structure of a central cross of the spherical hinge, and a structure of the assembling;

DETAILED DESCRIPTION OF THE EMBODIMENTS

Figure 1:
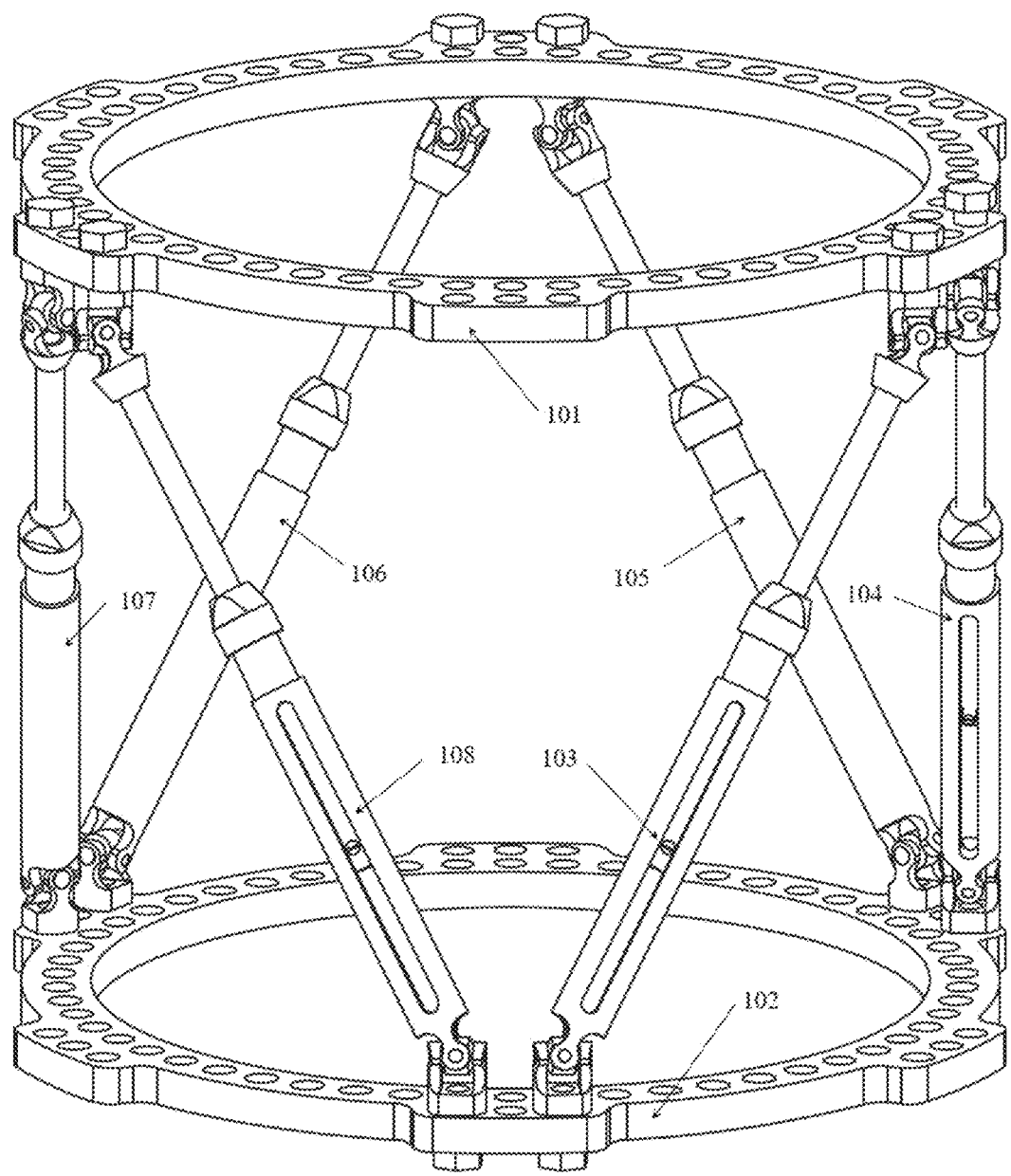
FIG. 1 illustrates a common structural schematic view of the existing six-chain ring-shaped parallel fixator.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout. The embodiments of the present invention will be described below in detail with reference to the drawings.

A fracture reduction method provided by the present invention is applicable to fracture reduction or limb deformity osteotomy and correction by using the existing six-chain ring-shaped parallel external fixator (such as patent CN201120414672, U.S. Pat. No. 8,454,604 or 6,030,386) or a parallel external fixator provided by the present invention. The external fixator generally has a structure illustrated in FIG. 1 and consists of a proximal fixation ring 101, a distal fixation ring 102, and a first strut 103, a second strut 104, a third strut 105, a fourth strut 106, a fifth strut 107 and a sixth strut 108 connected between the proximal fixation ring 101 and the distal fixation ring 102.

Figure 2:
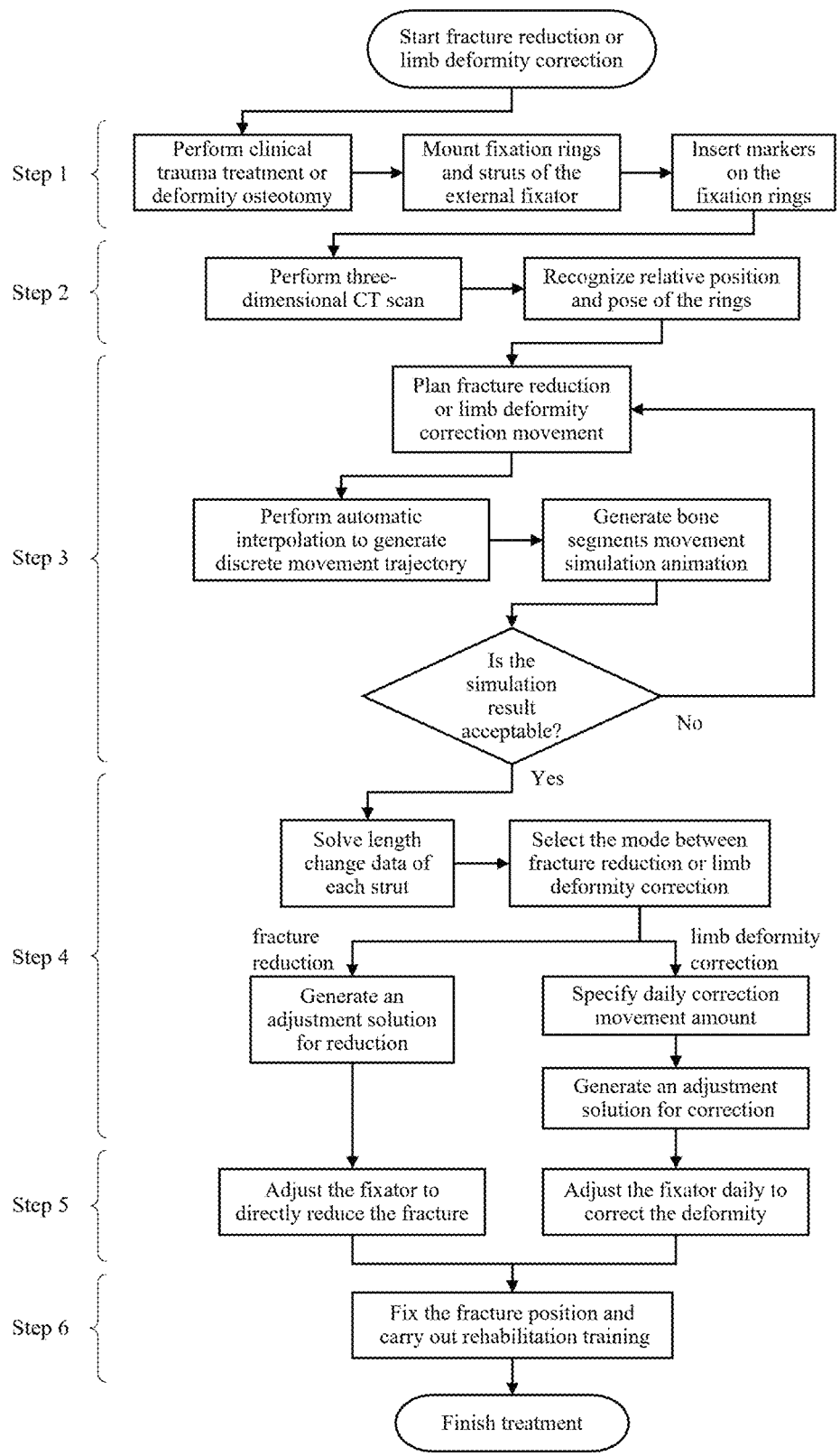
FIG. 2 illustrates a flowchart of a fracture reduction method according to the present invention.

As illustrated in FIG. 2, the fracture reduction method provided by the present invention specifically comprises the following steps.

Figure 3:
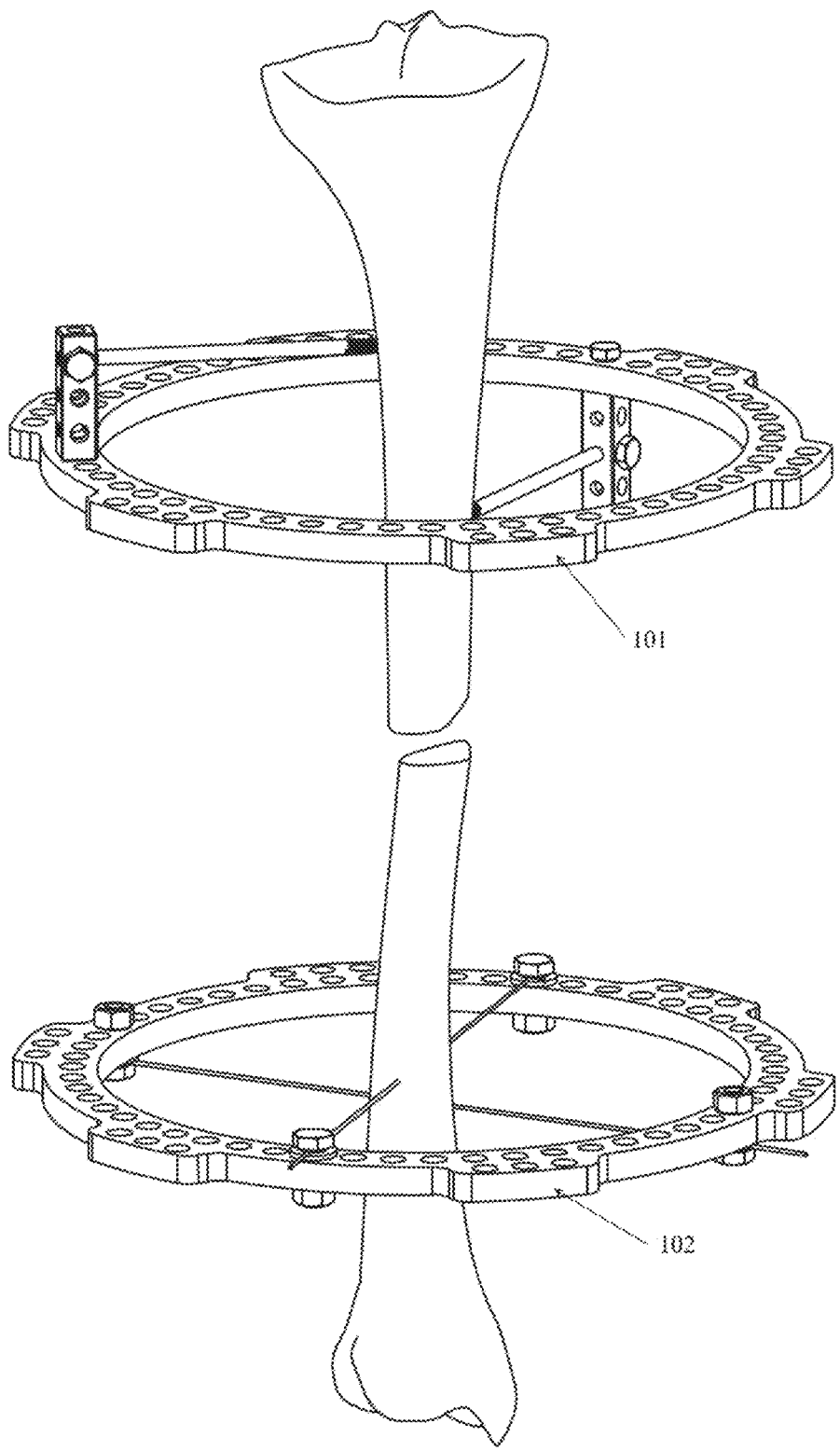
FIG. 3 illustrates a working view after two fixation rings of the existing six-chain ring-shaped fixator are respectively connected with bone segments at two sides of a fracture position.

(1) An external fixator is mounted according to the following steps:

(1a) For a patient with a fracture or limb deformity, after clinical trauma treatment or deformed bone osteotomy, a proximal bone segment and a distal bone segment at the fracture position are fixedly connected respectively with a proximal fixation ring 101 and a distal fixation ring 102 of an external fixator. As illustrated in FIG. 3, the proximal fixation ring 101 is fixedly connected with the proximal bone segment, and the distal fixation ring 102 is fixedly connected with the distal bone segment by several bone pins and bone pin connecting parts.

Figure 4:
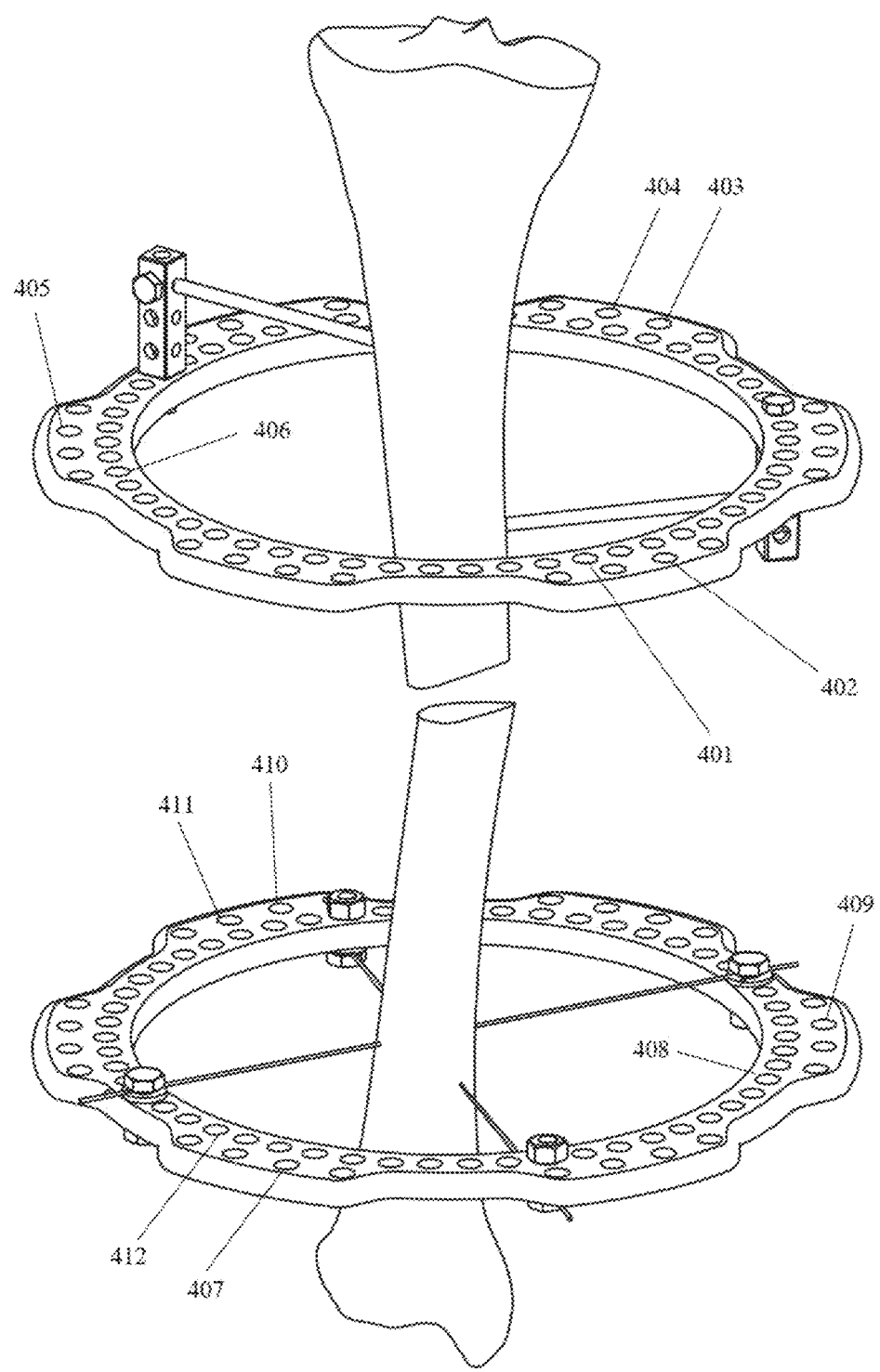
FIG. 4 illustrates a working view after two fixation rings of an external fixator of the present invention are respectively connected with bone segments at two sides of a fracture position.

(1b) A first strut 103 to a sixth strut 108 are connected between the proximal fixation ring and the distal fixation ring. The struts may be mounted symmetrically according to the method provided by patent CN201120414672, U.S. Pat. No. 8,454,604, or 6,030,386. When the device provided by the present invention is adopted, the struts may be freely connected within a certain mounting range (refer to FIG. 4), i.e., a first upper connecting hole 401, a second upper connecting hole 402, a third upper connecting hole 403, a fourth upper connecting hole 404, a fifth upper connecting hole 405 and a sixth upper connecting hole 406 in the proximal fixation ring 101 of the fixator are respectively selected for connecting threaded shafts at upper parts of the six struts; a first lower connecting hole 407, a second lower connecting hole 408, a third lower connecting hole 409, a fourth lower connecting hole 410, a fifth lower connecting hole 411 and a sixth lower connecting hole 412 in the distal fixation ring 102 of the fixator provided by the present invention are respectively selected for connecting threaded shafts at the lower parts of the six struts, and the selected twelve connecting holes should make the six struts arranged in a folded line around the circumference direction of the fixation rings, and be not in parallel with each other, and not intersect with each other. According to the method illustrated in FIG. 5, the six struts are sequentially mounted between the selected connecting holes. As an example, in the process of mounting the first strut 103, the first upper connecting hole 401 is selected, and the threaded shaft of the upper part of the first strut 103 inserts into the first upper connecting hole and is fixedly connected by using a nut 501; the first lower connecting hole 407 is selected, and the threaded shaft of the lower part of the first strut 103 inserts into the first lower connecting hole and is fixedly connected by using a nut 502; the upper part 503 and lower part 504 of the strut are connected by using a removable rod 2002 to complete the mounting of the first strut 103; and similarly, the second strut 104 to the sixth strut 108 are mounted. After the mounting of the external fixator provided by the present invention is completed, a mounting structure is as illustrated in FIG. 6.

Figure 5:
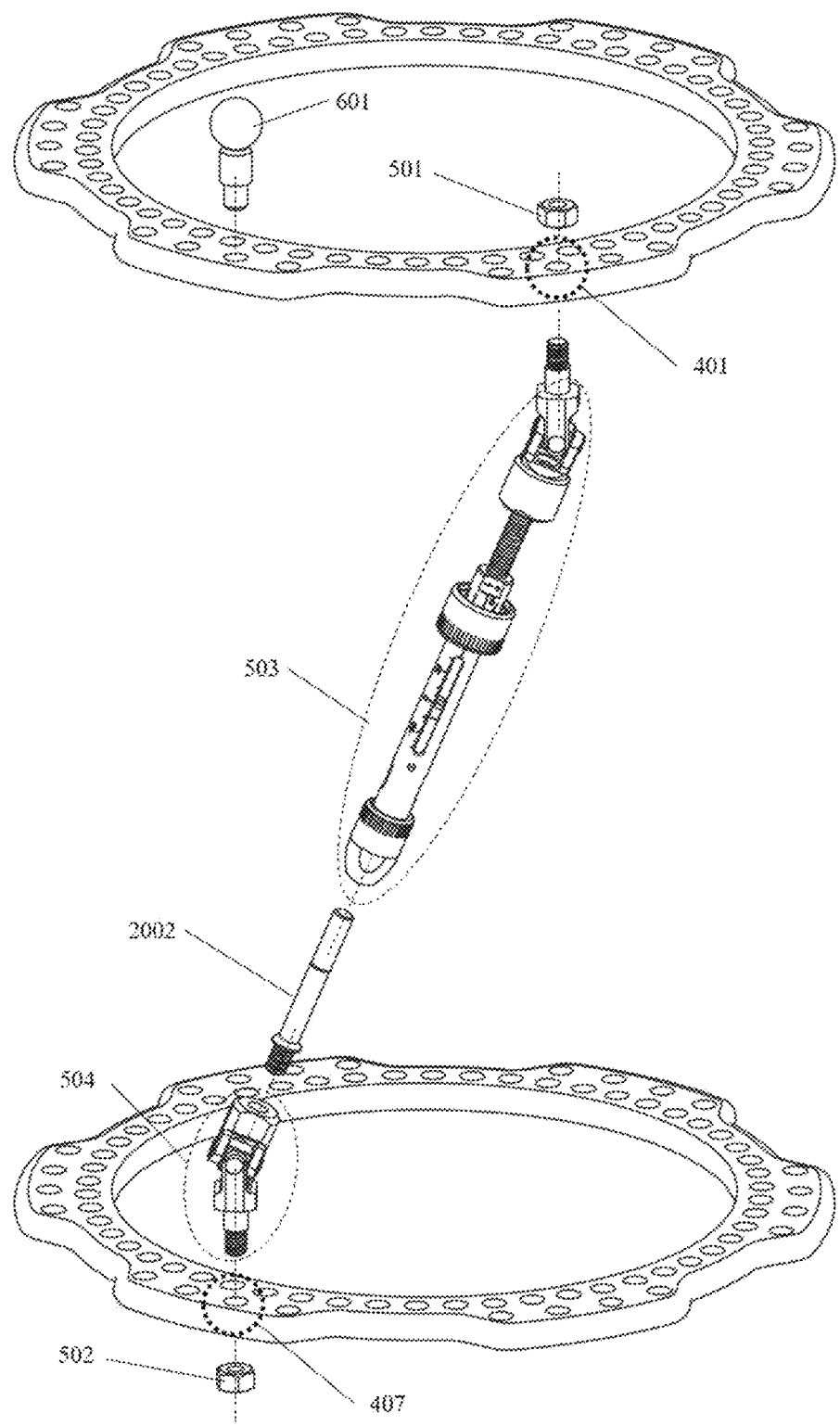
FIG. 5 illustrates a schematic view of a method for mounting a first strut and a first marker between a proximal fixation ring and a distal fixation ring of an external fixator of the present invention.
Figure 6:
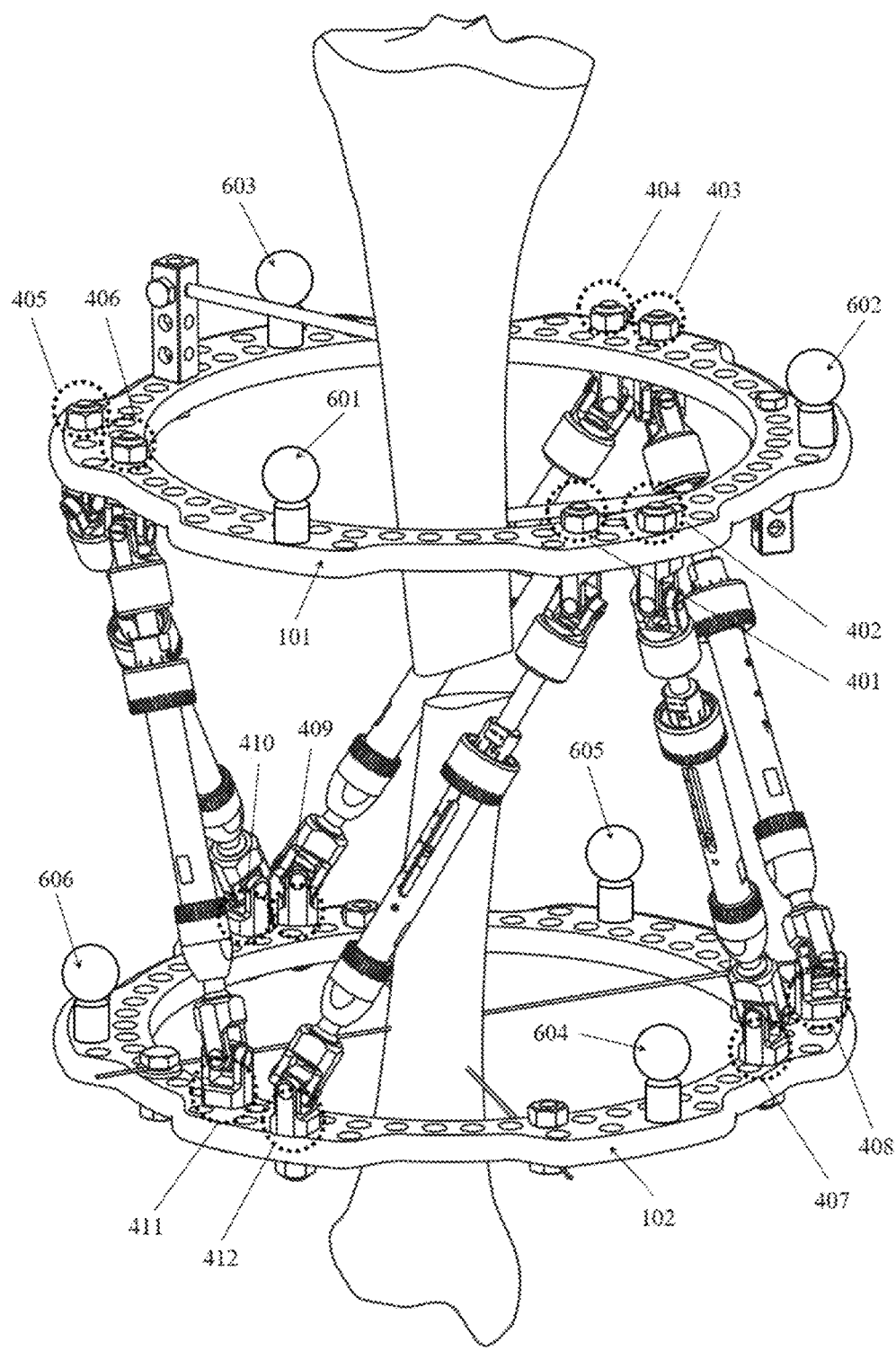
FIG. 6 illustrates an appearance view of an external fixator of the present invention in a clinical mounting completion condition.
Figure 7:
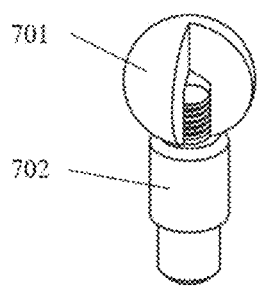
FIG. 7 illustrates a structural schematic view of a marker in the structure of the present invention.
Figure 9:
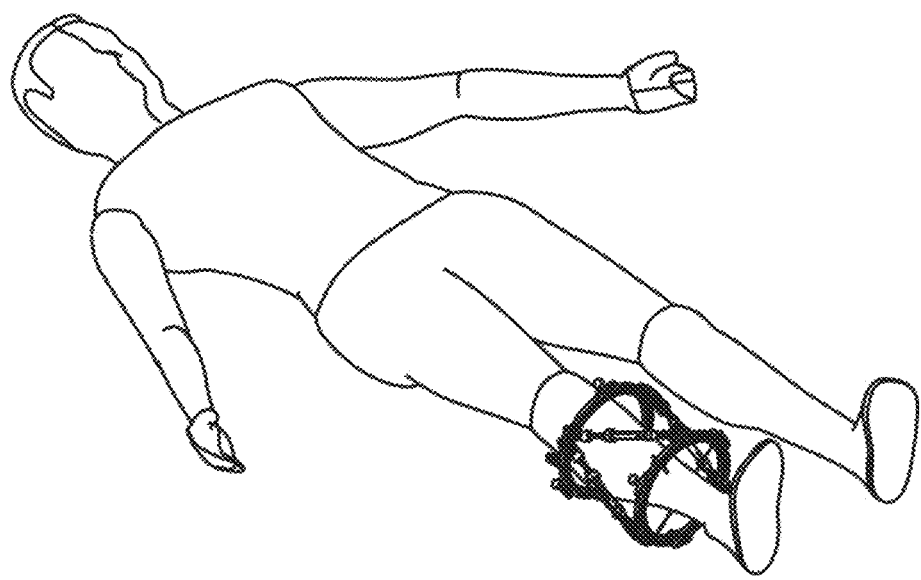
FIG. 9 illustrates an appearance view of a patient after the external fixator is mounted as FIG. 6.

(1c) Three connecting holes which are not connected with components and are distantly separate from each other in the proximal fixation ring 101 of the external fixator are selected, and a first marker 601 (as illustrated in FIG. 5), a second marker 602 and a third marker 603 are respectively inserted to form a fixed connection between the proximal fixation ring 101 and each marker; three connecting holes which are not used and are distantly separate from each other in the distal fixation ring 102 are selected, and a fourth marker 604, a fifth marker 605 and a sixth marker 606 are respectively inserted to form a fixed connection between the distal fixation ring 102 and each marker; and a mounting structure of the six markers on the fixator is as illustrated in FIG. 6. The six markers have the same structure and respectively comprise a marker ball 701 with an internal threaded hole and a marker pin shaft 702 (refer to FIG. 7) in threaded connection with the marker ball 701. The marker pin shaft 702 is capable of being directly inserted into the connecting hole of the fixation ring to form a fixed connection. The marker ball 701 is made of a metal material, and the marker pin shaft 702 is made of a plastic material. FIG. 9 shows an appearance view of a patient after the external fixator and the markers are mounted.

Figure 8:
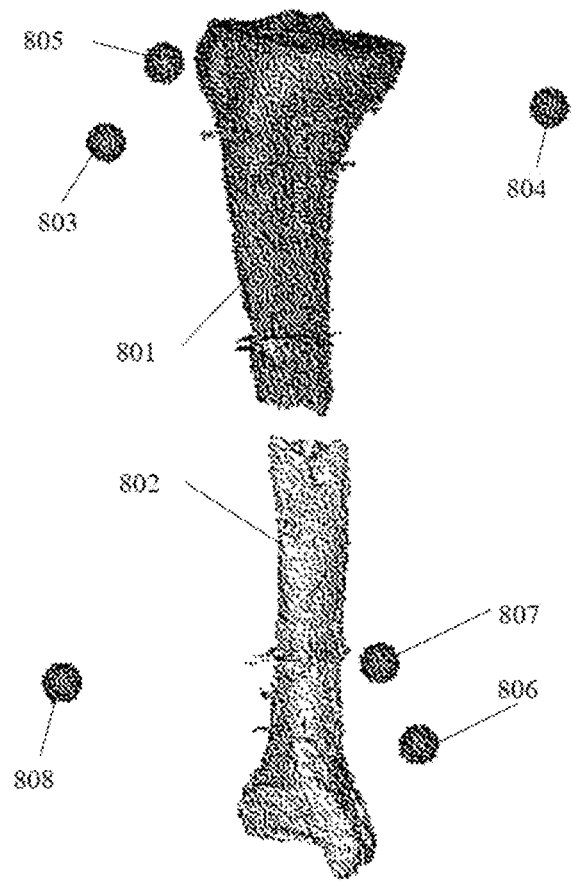
FIG. 8 illustrates a three-dimensional image obtained after scanning is performed by using a three-dimensional medical CT imaging device.

(2) Position and pose information is recognized according to the following steps:

(2a) The fracture position and the entire external fixator are scanned by using an existing three-dimensional medical CT imaging device, image processing and three-dimensional reconstruction are performed such that the six marker balls 701 are recognized to form a first three-dimensional sphere 803, a second three-dimensional sphere 804, a third three-dimensional sphere 805, a fourth three-dimensional sphere 806, a fifth three-dimensional sphere 807 and a sixth three-dimensional sphere 808, while the marker pin shaft 702 is not recognized (refer to FIG. 8), to obtain a three-dimensional image including a proximal bone segment three-dimensional solid 801, a distal bone segment three-dimensional solid 802, the first three-dimensional sphere 803, the second three-dimensional sphere 804, the third three-dimensional sphere 805, the fourth three-dimensional sphere 806, the fifth three-dimensional sphere 807 and the sixth three-dimensional sphere 808, and the three-dimensional image is stored in a computer system.

(2b) An operator specifies a corresponding relationship between the first three-dimensional sphere 803 to the sixth three-dimensional sphere 808 and the first marker 601 to the sixth marker 606 on the external fixator in the three-dimensional image by using a computer operating interface.

(2c) The computer system recognizes the center positions of the first three-dimensional sphere 803 to the sixth three-dimensional sphere 808 in the three-dimensional image by using a sphere fitting algorithm, and determines the position and pose of the proximal fixation ring 101 in the three-dimensional image by using the center positions of the first three-dimensional sphere 803, the second three-dimensional sphere 804 and the third three-dimensional sphere 805; and similarly determines the position and pose of the distal fixation ring 102 in the three-dimensional image by using the center positions of the fourth three-dimensional sphere 806, the fifth three-dimensional sphere 807 and the sixth three-dimensional sphere 808.

(2d) The computer solves and records the relative position and pose information of the proximal fixation ring 101 and the distal fixation ring 102 in the initial mounting condition by using a kinematic algorithm in the robotic field, then the first marker 601 to the sixth marker 606 are removed after the recognition.

Figure 10:
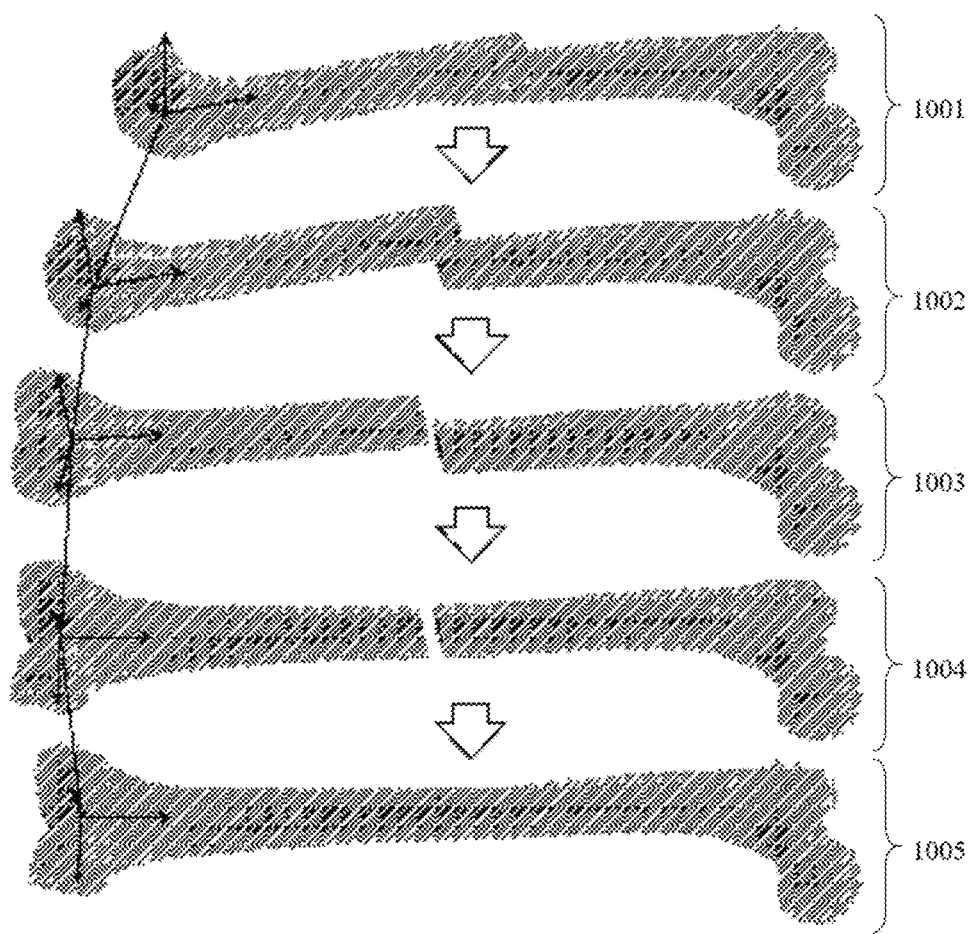
FIG. 10 illustrates a schematic view of the relative movement of fractured bone segments corresponding to the steps of fracture reduction method of the present invention.

(3) Fracture reduction or limb deformity correction movement is planned according to the following steps:

(3a) The proximal bone segment three-dimensional solid 801 and the distal bone segment three-dimensional solid 802 are observed in the computer operating interface, and the relative spatial states of the proximal bone segment three-dimensional solid 801 and the distal bone segment three-dimensional solid 802 are adjusted by using input devices such as a keyboard and a mouse according to expected fracture reduction or limb deformity correction plan, so as to form fracture reduction or limb deformity correction movement steps (such as movement step 1001, movement step 1002, movement step 1003, movement step 1004 and movement step 1005 in FIG. 10).

(3b) The computer system sequentially records the relative position and pose information of the proximal fixation ring 101 and the distal fixation ring 102 in each movement step, so as to determine the relative spatial state between the proximal bone segment and the distal bone segment. The computer calculates the variation of the relative position and pose information of the proximal fixation ring 101 and the distal fixation ring 102 between current movement step and the previous movement step, and automatically performs interpolation to obtain a discrete movement trajectory of fracture reduction or limb deformity correction.

(3c) the computer system draws the animation simulation of the relative movement of the proximal bone segment three-dimensional solid 801 and the distal bone segment three-dimensional solid 802 of the fracture in the operating interface based on the discrete movement trajectory. The operator checks whether the animation simulation meets the expected movement and whether there is a collision between the fractured bone segments. If the simulation result is unsatisfactory, the process returns to the beginning of step (3a) to design movement steps again; and if the simulation result is acceptable, the computer system stores the discrete movement trajectory of fracture reduction or limb deformity correction.

(4) Solving is performed to obtain an adjustment solution, wherein a solving method comprises the following steps: according to the stored discrete movement trajectory obtained in step (3), the computer system solves the length data of the first strut 103 to the sixth strut 108 at each discrete point of the discrete movement trajectory by using a kinematic algorithm of parallel mechanisms in the robotic field, then stores the struts length data in a discrete points struts length matrix. A "fracture reduction" mode or a "limb deformity correction" mode is selected in the computer operating interface according to the treatment type of a patient. In the "fracture reduction" mode, the computer reads the struts length data at each fracture reduction movement step from the discrete points struts length matrix, then arranges the struts length data according to the sequence of the movement steps to form an adjustment solution for fracture reduction. In the "limb deformity correction" mode, the operator sets the maximum daily displacement for limb deformity correction according to the distraction osteogenesis principle in the field of orthopedics (refer to U.S. Pat. No. 4,978,348); the computer selects several discrete points from the limb deformity correction movement trajectory according to the sequence of the movement steps and by taking the maximum daily displacement for limb deformity correction as the maximum interval, to form daily limb deformity correction trajectory points; and selects the struts length data from the discrete points struts length matrix according to the daily limb deformity correction trajectory points, and performs arrangement to form an adjustment solution for limb deformity correction.

The adjustment solution solving method at this step is described in detail below by adopting a specific embodiment: in the "fracture reduction" mode, for the movement steps planned in step (3) (such as movement step 1001, movement step 1002, movement step 1003 and movement step 1004 and movement step 1005 in FIG. 10), solving is performed to obtain the length data of the first strut 103 to the sixth strut 108 at each movement step, and the struts length data are then sequentially arranged to form an adjustment solution as shown in Table 1. In the "limb deformity correction" mode, for the movement steps planned in step (3), the maximum daily displacement for limb deformity correction is set as 1 mm, and then several points are selected from the discrete movement trajectory of limb deformity correction at the maximum interval of 1 mm, forming the daily limb deformity correction points (for example, in the process of movement step 1 to movement step 2, the relative spatial displacement of fractured bone segments is 4.83 mm, and five days of adjustment are needed for completing deformity correction movement from step 1 to step 2; thus from the discrete movement trajectory for step 1 to step 2, four discrete points are sequentially selected at an interval of 1 mm displacement as the spatial points to be reached every day by the bone segments from the 1st day to the 4th day; a next trajectory point is selected at an interval of 0.83 mm displacement from the discrete movement trajectory as the spatial position to be reached by the bone segments on the 5th day; for the rest correction process, see Table 2; according to the above-mentioned daily limb deformity correction points, the computer reads the struts length data from the discrete points struts length matrix to form an adjustment solution for limb deformity correction, as shown in Table 2.

TABLE 1

Adjustment solution for fracture reduction

| Movement step | First strut | Second strut | Third strut | Fourth strut | Fifth strut | Sixth strut |
|---|---|---|---|---|---|---|
| 1 | 108.5 mm | 112.4 mm | 131.0 mm | 127.3 mm | 118.8 mm | 106.5 mm |
| 2 | 110.1 mm | 113.5 mm | 133.9 mm | 131.2 mm | 120.1 mm | 109.1 mm |
| 3 | 113.0 mm | 115.6 mm | 134.8 mm | 134.0 mm | 122.5 mm | 110.4 mm |
| 4 | 113.8 mm | 115.0 mm | 136.4 mm | 134.6 mm | 122.9 mm | 111.2 mm |
| 5 | 110.6 mm | 113.2 mm | 132.8 mm | 130.4 mm | 119.6 mm | 109.2 mm |

TABLE 2

Adjustment solution for limb deformity correction

| Movement step | Correction data | First strut | Second strut | Third strut | Fourth strut | Fifth strut | Sixth strut | Daily interval |
|---|---|---|---|---|---|---|---|---|
| 1-2 | 1st day | 108.5 mm | 112.4 mm | 131.0 mm | 127.3 mm | 118.8 mm | 106.5 mm | — |
|  | 2nd day | 109.0 mm | 112.7 mm | 131.8 mm | 128.3 mm | 119.2 mm | 107.2 mm | 1 mm |
|  | 3rd day | 109.5 mm | 113.0 mm | 132.6 mm | 129.3 mm | 119.6 mm | 107.9 mm | 1 mm |
|  | 4th day | 110.0 mm | 113.3 mm | 133.4 mm | 130.3 mm | 119.8 mm | 108.6 mm | 1 mm |
|  | 5th day | 110.1 mm | 113.5 mm | 133.9 mm | 131.2 mm | 120.1 mm | 109.1 mm | 0.83 mm |
| 2-3 | 6th day | 111.1 mm | 114.3 mm | 114.2 mm | 132.2 mm | 121.0 mm | 109.6 mm | 1 mm |
|  | 7th day | 112.1 mm | 115.1 mm | 114.6 mm | 133.2 mm | 121.9 mm | 110.1 mm | 1 mm |
|  | 8th day | 113.0 mm | 115.6 mm | 134.8 mm | 134.0 mm | 122.5 mm | 110.4 mm | 0.82 mm |
| 3-4 | 9th day | 113.6 mm | 115.4 mm | 135.8 mm | 134.4 mm | 122.8 mm | 110.9 mm | 1 mm |
|  | 10th day | 113.8 mm | 115.0 mm | 136.4 mm | 134.6 mm | 122.9 mm | 111.2 mm | 0.21 mm |
| 4-5 | 11th day | 112.9 mm | 114.5 mm | 135.5 mm | 133.5 mm | 122.0 mm | 110.7 mm | 1 mm |
|  | 12th day | 112.0 mm | 114.0 mm | 134.6 mm | 132.4 mm | 121.1 mm | 110.2 mm | 1 mm |
|  | 13th day | 111.1 mm | 113.5 mm | 133.7 mm | 131.3 mm | 120.2 mm | 109.7 mm | 1 mm |
|  | 14th day | 110.6 mm | 113.2 mm | 132.8 mm | 130.4 mm | 119.6 mm | 109.2 mm | 0.91 mm |

(5) Adjust the external fixator by the following steps: when the existing external fixator is used, according to the mode selected in step (4), for the "fracture reduction" mode, according to the struts length data given by the adjustment solution for fracture reduction obtained in step (4), the lengths of the six struts 103-108 are adjusted (for the method for adjusting the lengths of struts, refer to the corresponding patent for the existing external fixator, such as patent CN201120414672, U.S. Pat. No. 8,454,604 or 6,030,386) such that the external fixator directly reduces the fracture. For the "limb deformity correction" mode, according to the adjustment solution for limb deformity correction obtained in step (4), the lengths of the six struts 103-108 are adjusted daily such that the external fixator gradually corrects the limb deformity within a certain period of time.

Figure 19:
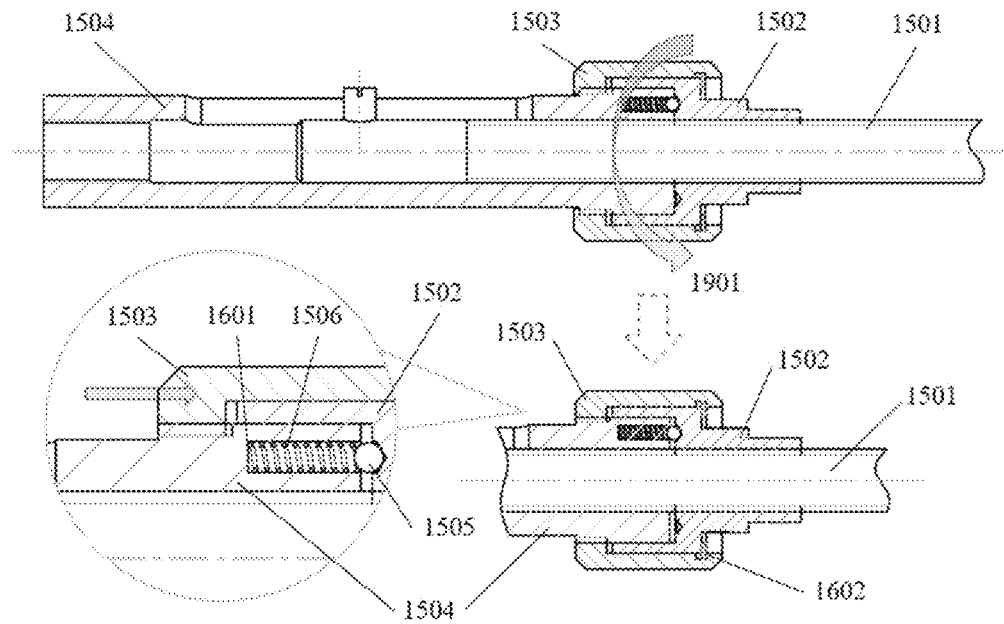
FIG. 19 illustrates a schematic view of a method for switching the working state of a driving joint of the strut.

In order to make the adjustment process of the external fixator more precise and effective, the external fixator provided by the present invention has a driving joint locking function. The adjustment method of the present invention will be described in detail with the parallel external fixator in the present invention. For the "fracture reduction" mode, the locking rings 1503 of the first strut 103 to the sixth strut 108 are anticlockwise rotated relative to the sliding sleeve 1504 (refer to FIG. 19), and the threaded fit between the locking rings 1503 and the sliding sleeve 1504 makes a gasket 1602 to loosen the driving nut 1502, such that the driving joints 1302 (refer to FIG. 13) of the first strut 103 to the sixth strut 108 are placed in the "adjustable" working state; according to the adjustment solution for fracture reduction, the driving nuts 1502 of the first strut 103 to the sixth strut 108 are rotated to change the length of each strut, and the proximal fixation ring 101 and the distal fixation ring 102 of the external fixator move relative to each other to reduce the fracture; the locking ring 1503 of the first strut 103 to the sixth strut 108 is clockwise rotated relative to the sliding sleeve 1504, and the locking ring 1503 drives the gasket 1602 to press the driving nut 1502, such that the driving joints 1302 are placed in the "locked" working state, fixing the fracture bone segments. For the "limb deformity correction" mode, the lengths of the struts are adjusted daily. The adjusting method is that the driving joints 1302 of the first strut 103 to the sixth strut 108 are placed in the "adjustable" working state (according to the method mentioned above); according to the strut length adjustment solution for limb deformity correction, the driving nuts 1502 of the first strut 103 to the sixth strut 108 are rotated to change the length of each strut; the proximal fixation ring 101 and the distal fixation ring 102 of the external fixator move relatively to correct the limb deformity for the amount for that day; then the locking ring 1503 of the first strut 103 to the sixth strut 108 is clockwise rotated relative to the sliding sleeve 1504, and the locking ring 1503 drives the gasket 1602 to press the driving nut 1502, such that the driving joint 1302 is placed in the "locked" working state, temporarily fixing deformed bone segments; and the above operation is repeated every day till the limb deformity correction is completed.

Figure 23:
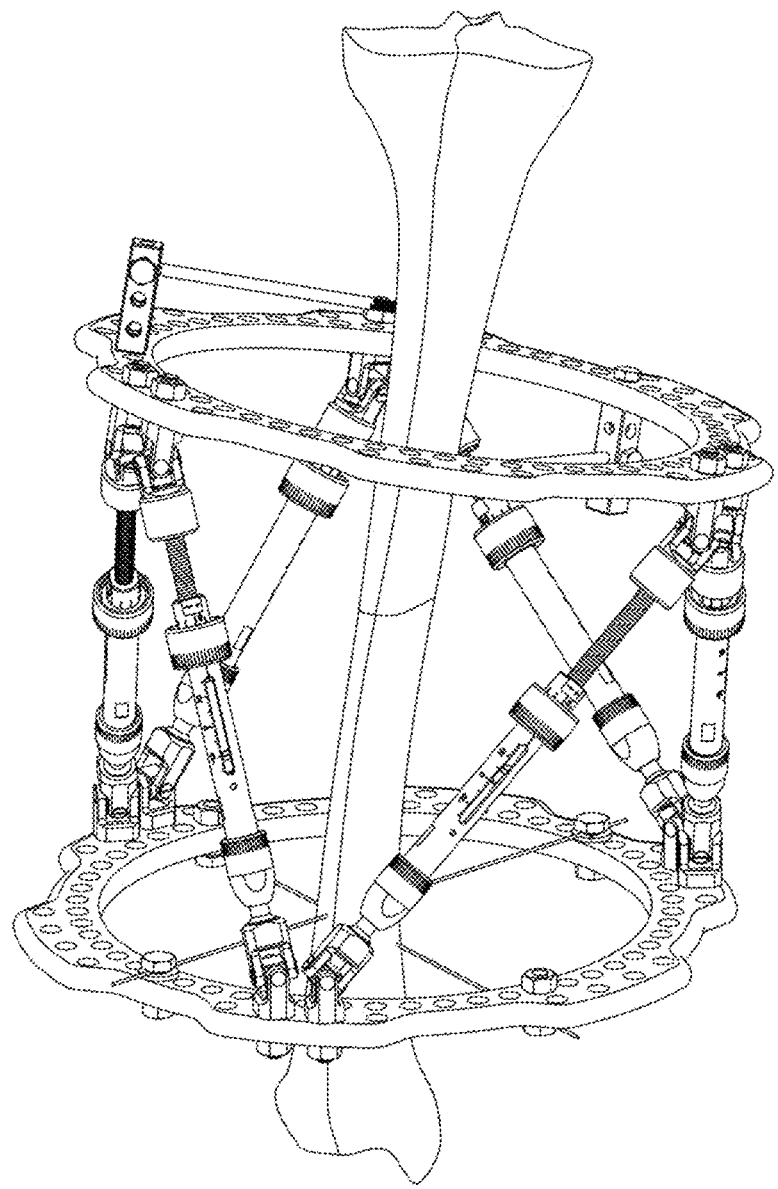
FIG. 23 illustrates a schematic appearance view after fracture reduction or limb deformity correction is performed by using an external fixator provided by the present invention.

(6) After fracture reduction or limb deformity correction (an appearance of the external fixation device provided by the present invention is as illustrated in FIG. 23) is completed, the lengths of the six struts of the external fixation device are locked till the healing of the fracture or limb deformity is complete, and the external fixator is removed to finish the treatment of fracture or limb deformity.

Figure 11:
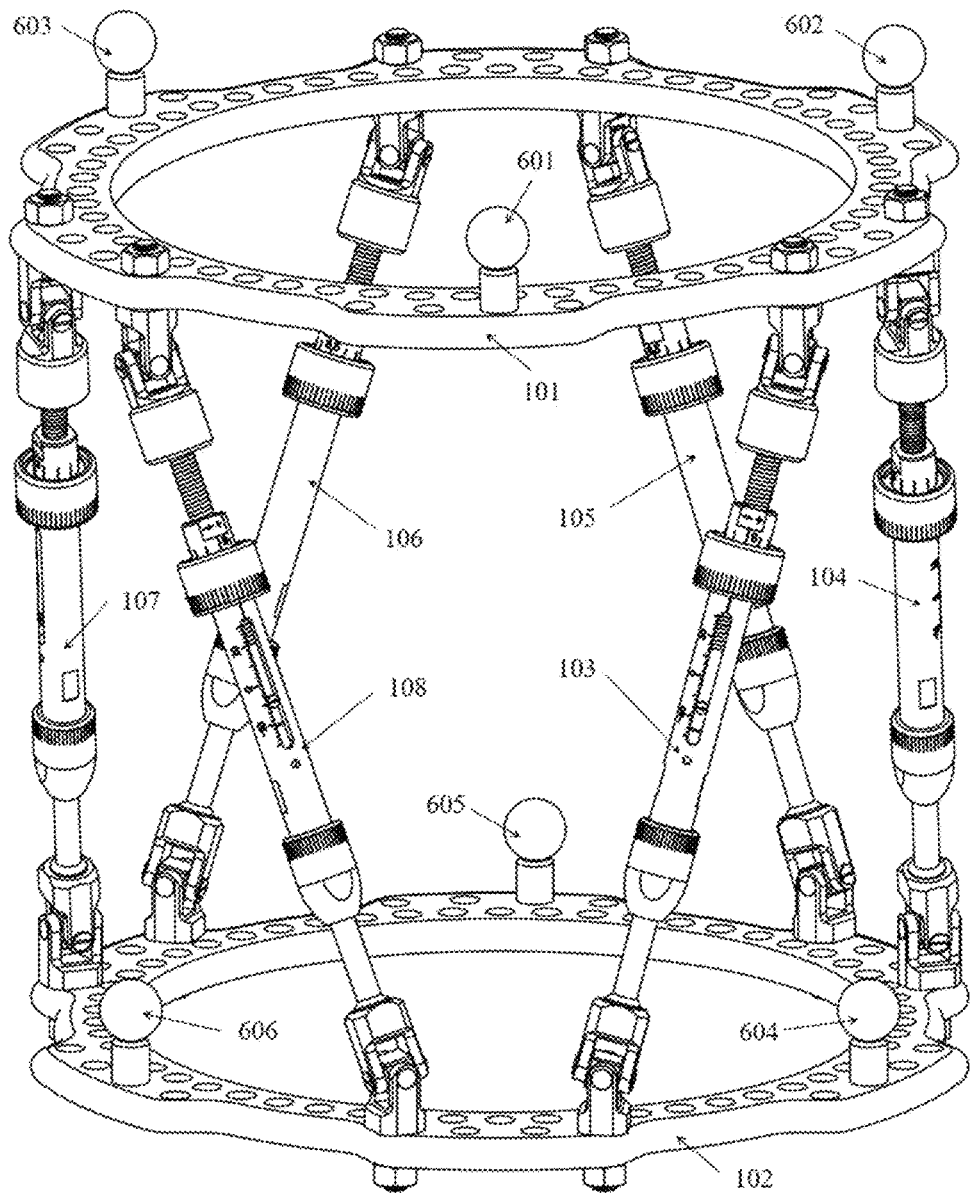
FIG. 11 illustrates a structural schematic view of a parallel external fixator of the present invention.
Figure 12:
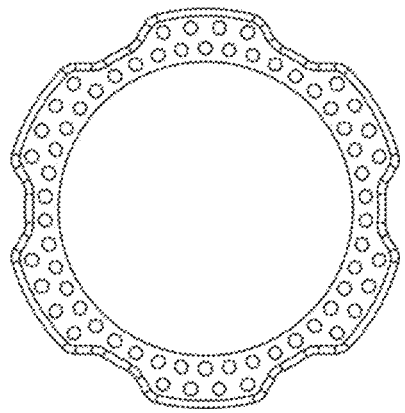
FIG. 12A, FIG. 12B, FIG. 12C and FIG. 12D illustrate structural schematic views of a proximal fixation ring and a distal fixation ring.
Figure 12:
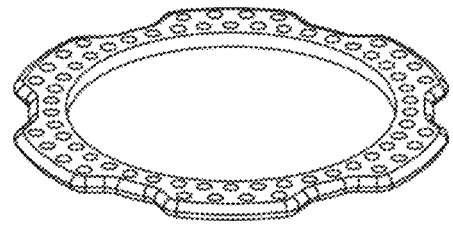
Figure 12:
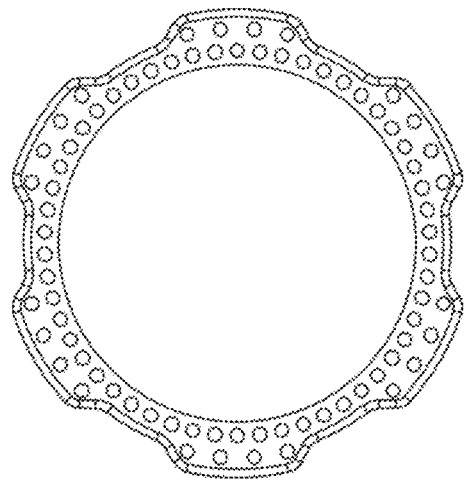
Figure 12:
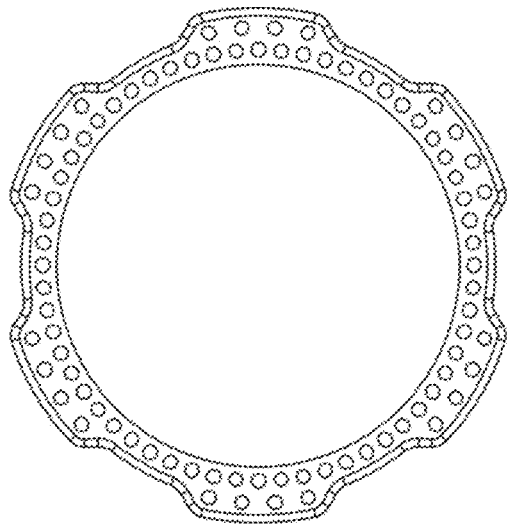

In order to better realize the method provided by the present invention, the present invention provides a parallel external fixator, which can be embodied in the type illustrated in FIG. 11, comprising:

a proximal fixation ring 101 and a distal fixation ring 102 provided below the proximal fixation ring 101, wherein the proximal fixation ring 101 and the distal fixation ring 102 have the same ring structure (refer to FIG. 12), six protrusions are uniformly provided at an interval on the sidewall of the ring structure, a plurality of inner ring connecting holes with axis in a vertical direction are uniformly provided at an interval in the entire ring structure, and outer ring connecting holes axially-oriented along the vertical direction are uniformly provided at an interval in the protrusions. The proximal fixation ring 101 and the distal fixation ring 102 are available in different diameters (refer to FIG. 12). The operator can select fixation rings with suitable diameter for the needs of different patients and use the fixation rings as the proximal fixation ring 101 and distal fixation ring 102 of the external fixator respectively. Preferably, the upper and lower edges of the proximal fixation ring 101 and the distal fixation ring 102 are subjected to filleting treatment.

Figure 13:
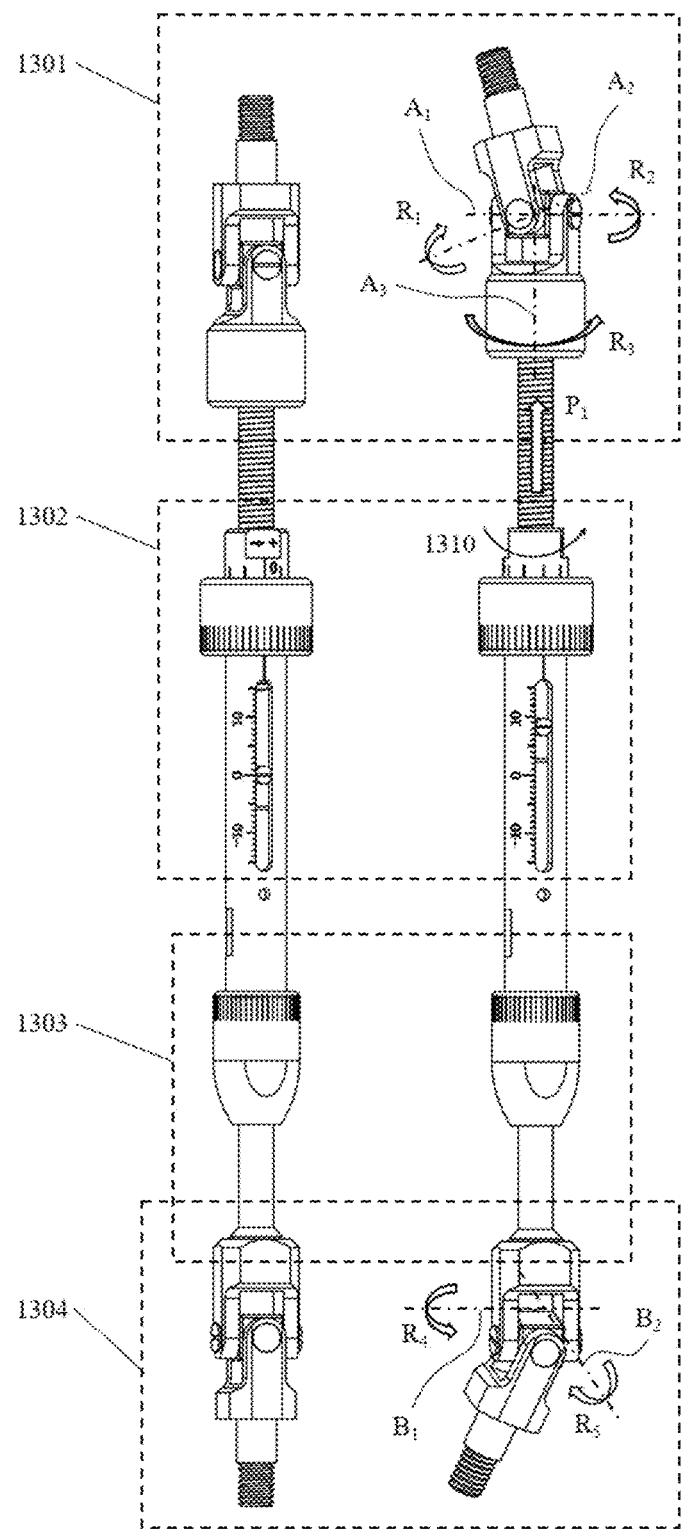
FIG. 13 illustrates a structural schematic view of a strut.

Six struts with the same structure are provided between the proximal fixation ring 101 and the distal fixation ring 102, as illustrated in FIG. 11, respectively including a first strut 103, a second strut 104, a third strut 105, a fourth strut 106, a fifth strut 107 and a sixth strut 108. The six struts are capable of being freely configured according to the following rules: the first strut to the sixth strut are sequentially provided around the circumferential direction of the fixation ring, and every two adjacent struts are not in parallel with each other and do not intersect with each other. As illustrated in FIG. 13, each strut comprises a spherical hinge 1301, a driving joint 1302, a quick-mounting component 1303 and a universal hinge 1304, which are sequentially connected from top to bottom.

The spherical hinge 1301 is a ball joint part with three degree-of-freedom commonly used in the field of mechanical connection, which structure is illustrated in FIG. 14A. The spherical rod joint 1410 at the upper part of the spherical hinge and the spherical sleeve part 1411 at the lower part thereof are connected in the form of spherical fit (for detailed structure, refer to the description of patent CN201380070568). Preferably, the structure of the spherical hinge 1301 is as illustrated in FIG. 14B, FIG. 14C and FIG. 14D, which provides a larger rotation workspace. The spherical hinge 1301 comprises a connecting shaft 1401 whose upper end is a threaded shaft, the threaded shaft of the connecting shaft 1401 is capable of inserting into an outer ring connecting hole (or an inner ring connecting hole) in the proximal fixation ring 101 and is fixedly connected with the proximal fixation ring 101 through a nut 501 (refer to FIG. 5), and the lower end of the connecting shaft 1401 is pivotally connected with the both ends of the long shaft 1403 of a cross-shaft component. The cross-shaft component is mounted at the upper part of a revolute connecting sleeve 1406, and the outer ends of the other two short shafts 1402 of the cross-shaft component are respectively and pivotally connected into the hole of the revolute connecting sleeve 1406. A plain bearing 1407 is pivotally mounted in the cavity of the lower part of the revolute connecting sleeve 1406, the inner ring of the plain bearing 1407 is in fixed connection with the upper section of a screw rod 1501, where the top of the screw rod 1501 inserts into the plain bearing 1407 and is fixedly connected with an anti-loosening nut 1405 to prevent the threaded connection between the plain bearing 1407 and the screw rod 1501 from loosening. A back nut 1408 is connected with the internal thread at the bottom of the cavity of the revolute connecting sleeve 1406 through an external thread, a certain gap is formed between the outer surface of the screw rod 1501 and the inner hole of the back nut 1408, and the screw rod and the back nut are capable of rotating freely and relatively. The back nut 1408 plays a role of axially positioning the plain bearing 1407.

Figure 15:
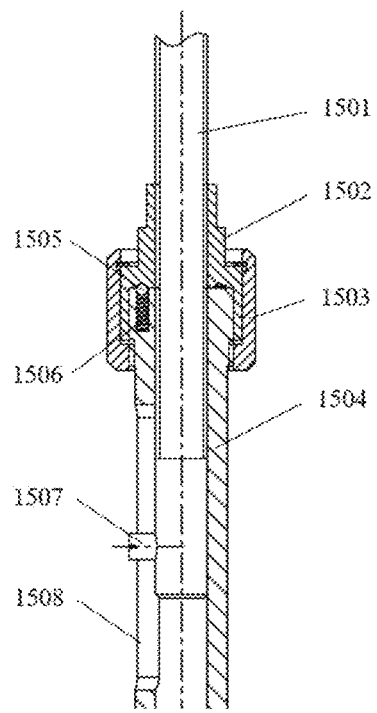
FIG. 15 illustrates a schematic view of a sectional structure of a driving joint of the strut.
Figures 16A, 16B:
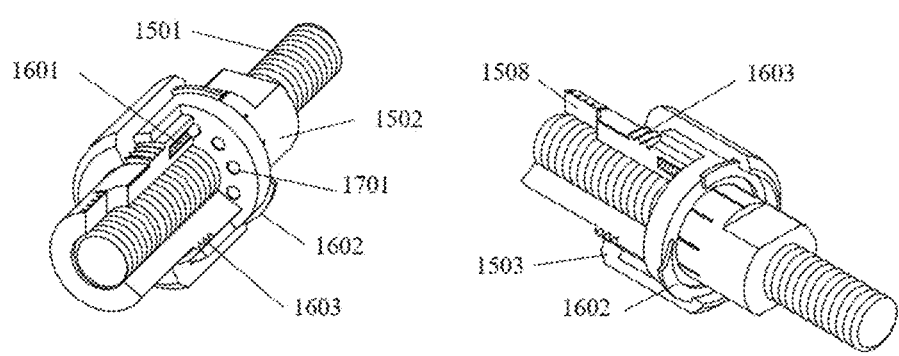
FIG. 16 illustrate schematic views of sectional structures at two different viewing orientations of a driving joint of the strut.
Figure 17A:
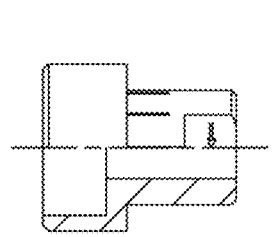
FIG. 17A and FIG. 17B respectively illustrate a frontal view and a lateral view of a strut driving nut structure.
Figure 17B:
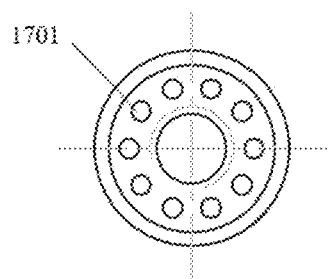
Figure 17C:
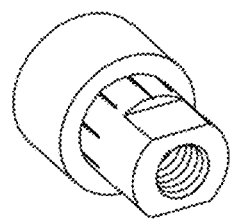
FIG. 17C illustrates a three-dimensional view of a strut driving nut structure.
Figure 18:
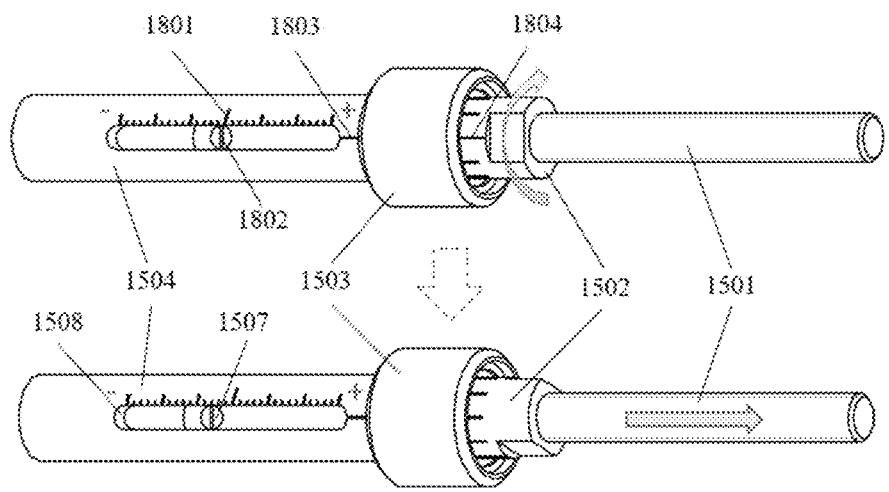
FIG. 18 illustrates a schematic view of a method for adjusting the length of a strut by using a driving joint of the strut.

As illustrated in FIG. 15, the driving joint 1302 is a screw mechanism, and the lower screw section of the screw rod 1501 sequentially inserts into the middle threaded hole of a driving nut 1502 and the middle hole of a sliding sleeve 1504. The screw rod 1501 and the driving nut 1502 form a screw pair. The driving nut 1502 comprises a cylindrical part, a boss with a diameter smaller than the diameter of the cylindrical part provided on the top wall of the cylindrical part, the upper part of the sliding sleeve 1504 is inserted in the cylindrical part and is in rotary fit with the inner wall of the cavity of the cylindrical part. A plurality of steel ball holes 1701 (refer to FIG. 16, FIG. 17A, FIG. 17B, and FIG. 17C) with axis in the vertical direction are uniformly provided at an interval in the circumferential direction on the top wall of the cavity of the cylindrical part, a spring hole 1601 corresponding to a steel ball hole 1701 is provided in the top surface of the sliding sleeve 1504, a spring 1506 is mounted in the spring hole 1601, the bottom end of the spring 1506 is connected with the bottom wall of the spring hole 1601 and a steel ball 1505 is fixed at the top end of the spring 1506; the depth of the steel ball hole 1701 is smaller than the radius of the steel ball 1505, and when the driving nut 1502 is rotating (refer to FIG. 19), the steel ball 1505 is periodically and partially embedded into or withdrawn from the steel ball hole 1701 under the effect of the spring 1506 to provide a vibration tactile feedback of rotary movement amount. An external thread 1603 is provided on the outer wall of the sliding sleeve 1504 located at the bottom of the cylindrical part, a locking ring 1503 sleeves the cylindrical part of the driving nut 1502, and the lower end of the locking ring 1503 is in thread connection with the external thread 1603 on the sliding sleeve 1504; a groove is provided in the inner wall of the cavity at the upper end of the locking ring 1503 and is embedded with a gasket 1602, and the gasket 1602 sleeves the boss of the driving nut 1502 and is in sliding contact with the top wall of the cylindrical part to limit the axial movement of the driving nut 1502 (refer to FIG. 16). The locking ring 1503 is capable of pressing the gasket 1602 or loosening the gasket 1602 by rotating the locking ring 1503. An observation slot 1508 is provided along the axial direction of the sidewall of the sliding sleeve 1504, and a telescoping scale mark 1801 (refer to FIG. 18) is provided along the axial direction of the sliding sleeve on the sidewall corresponding to the observation slot 1508; an axial scale mark 1803 is provided along the axial direction of the sliding sleeve at the top end of the observation slot 1508. The lower side screw section of the screw rod 1501 is provided with a pin shaft 1507, and the pin shaft 1507 is inserted into the observation slot 1508 and is capable of sliding relative to the observation slot 1508; the head face of the pin shaft 1507 is provided with a transverse scale mark 1802, the transverse scale mark 1802 and the telescoping scale mark 1801 are provided matching each other to indicate the elongation or shortening value of the strut length. A circumferential scale mark 1804 is provided on the outer wall of the boss of the driving nut 1502, the circumferential scale mark 1804, and the axial scale mark 1803 are provided matching each other to indicate the rotation value of the driving nut 1502 relative to the sliding sleeve 1504.

The driving joint 1302 has two working states of "adjustable" and "locked". The driving joint is at the "locked" working state in the initial mounting condition, wherein the locking ring 1503 presses the driving nut 1502 relative to the sliding sleeve 1504 along the axial direction through the gasket 1602, and the produced pressure makes the driving nut 1502 unable to rotate relative to the sliding sleeve 1504 so as to lock the driving joint. When the locking ring 1503 is anticlockwise rotated 1901 (refer to FIG. 19) relative to the sliding sleeve 1504, the threaded fit between the locking ring 1503 and the sliding sleeve 1504 enables the gasket 1602 to loosen the driving nut 1502, entering the "adjustable" working state. When the driving joint 1302 is at the "adjustable" working state, the driving nut 1502 can rotate freely, that is, the length of the strut can be increased by clockwise rotating the driving nut 1502 relative to the sliding sleeve 1504 (refer to FIG. 18), and the length of the strut can be shortened by anticlockwise rotating the driving nut 1502, thus forming the elongation/shortening movement of the strut. Through the indication of the telescoping scale mark 1801 and the transverse scale mark 1802, the integral value of the elongation/shortening movement can be read; through the axial scale mark 1803 and the circumferential scale mark 1804, the rotation value of the driving nut 1502 relative to the sliding sleeve 1504 can be read, and the decimal value of the elongation/shortening movement of the strut can be obtained through conversion.

Figure 20:
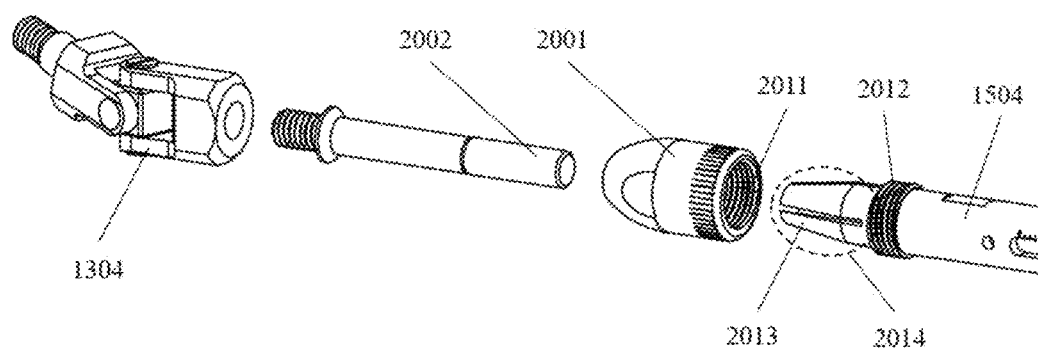
FIG. 20 illustrates a structural schematic view of a quick-mounting component of a strut.
Figure 21:
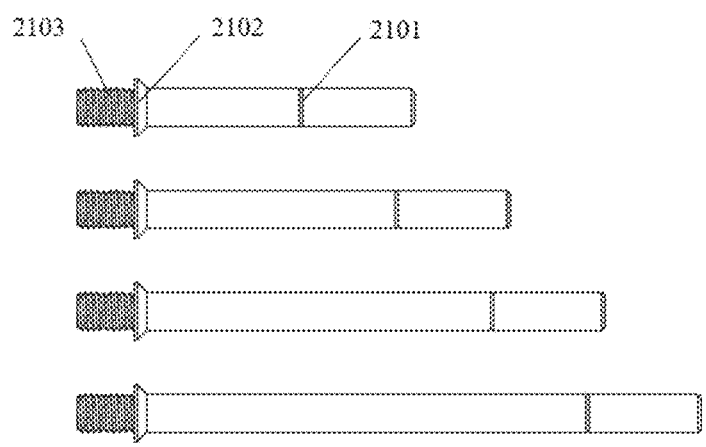
FIG. 21 illustrates a structural schematic view of removable rods with different lengths of a strut.

As illustrated in FIG. 20, the lower part of the sliding sleeve 1504 is connected with the upper part of a removable rod through the quick-mounting component 1303. As illustrated in FIG. 21, the upper part of the removable rod 2002 has a circle mark 2101, the lower part of the removable rod 2002 is provided with an external thread 2103, and preferably a positioning boss surface 2102 is provided between the external threaded rod 2103 section and the smooth rod section of the removable rod 2002; and the removable rod 2002 are available in different lengths. The external thread 2103 of the removable rod and the threaded hole in the upper part of a universal hinge 1304 (refer to FIG. 13 and FIG. 20) form a threaded connection. A threaded shaft at the lower part of the universal hinge 1304 inserts into an outer ring connecting hole (or an inner ring connecting hole) in the distal fixation ring 102 and is fixedly connected with the distal fixation ring 102 through a nut 502 (refer to FIG. 5). The universal hinge 1304 is a common universal joint part in the field of mechanical transmission components, and the universal hinge 1304 provides two rotational degrees of freedom (DoFs) between the removable rod 2002 and the distal fixation ring 102 connected at the two ends thereof.

As a preferred embodiment of the present invention, as illustrated in FIG. 20, the quick-mounting component 1303 comprises a locking sleeve 2001 with an inner hole, the upper end of the inner hole of the locking sleeve 2001 has an internal thread 2011, and the lower end is a conical hole; the lower part of the sliding sleeve 1504 has an external thread, the lower part of the external thread 2012 and a conical end 2013, and a plurality of notches are provided at an interval along the generatrix direction of the conical end 2013 to form an elastic locking jaw 2014; the sliding sleeve 1504 is in threaded fit with the internal thread of the locking sleeve 2001 through the external thread 2012, and the locking jaw 2014 of the sliding sleeve 1504 is in conical surface fit with the conical hole of the locking sleeve 2001. A smooth rod section at the head end of a removable rod 2002 passes through the inner hole of the locking sleeve 2001 and is inserted into the inner hole of the locking jaw 2014; by using the threaded fit between the sliding grove sleeve 1504 and the locking sleeve 2001 and the conical surface fit between the locking jaw 2014 of the sliding sleeve 1504 and the conical hole of the locking sleeve 2001, the fixed connection or disassembly of the removable rod 2002 and the sliding sleeve 1504 can be achieved. A specific operating method comprises the following steps: a removable rod 2002 with a suitable length is selected from a plurality of removable rods with different lengths (refer to FIG. 21), passes through the inner hole of the locking sleeve 2001 and is inserted into the inner hole of the locking jaw 2014; the locking jaw 2014 is inserted into the inner hole of the locking sleeve 2001, then the locking sleeve 2001 is anticlockwise rotated, under the effect of threaded fit and cone surface fit thereof, the diameter of the inner hole of the locking jaw 2014 is gradually decreased, so as to clamp the external surface of the removable rod 2002 to realize the fixed connection between the removable rod 2002 and the sliding sleeve 1504; and on the contrary, by clockwise rotating the locking sleeve 2001, the diameter of the inner hole of the locking jaw 2014 can be gradually increased, so as to loosen the removable rod 2002 to realize the disassembly of the removable rod 2002 and the sliding sleeve 1504.

Figure 22:
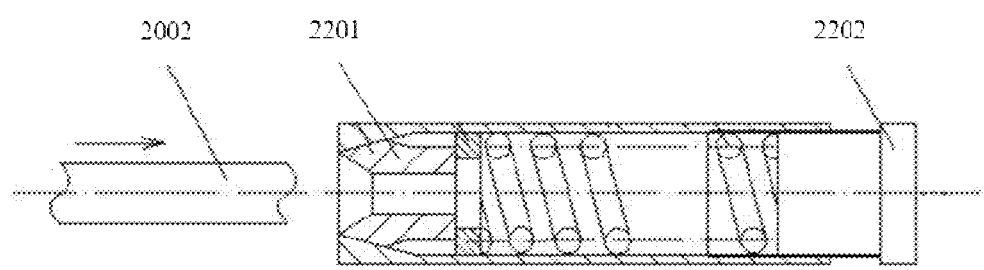
FIG. 22 illustrates a structural schematic view of another usable quick-mounting component of a strut.

The quick-mounting component 1303 may also be a chuck device capable of quickly clamping a shaft part. As illustrated in FIG. 22, one end 2202 of the quick-mounting component 1303 is connected with the sliding sleeve 1504; the smooth rod section of the front end 2002 of the quick-mounting component 1303 can stretch inside from the other end 2201 when the quick-mounting component 1303 is in a loosened state, and the quick-mounting component 1303 can clamp the inserted removable rod 2002 to form a fixed connection. The mechanical structure of the quick-mounting component is not limited to the above forms. For example, mechanical structures with a function of quickly clamping shaft parts in patent CN201711062794, CN201510692150 or the like may be adopted.

The external fixator provided by the present invention is further provided with a marker used for realizing accurate fracture reduction or limb deformity correction. Three connecting holes which are not connected with components and are distantly separate from each other in the proximal fixation ring 101 of the external fixator are selected, as illustrated in FIG. 5, and a first marker 601, a second marker 602 and a third marker 603 are respectively inserted to form a fixed connection; and three connecting holes which are not used and are distantly separate from each other in the distal fixation ring 102 are selected, and a fourth marker 604, a fifth marker 605 and a sixth marker 606 are respectively inserted to form a fixed connection. A mounting appearance after the six markers are mounted on the fixator is illustrated in FIG. 11. The six markers have the same structure and respectively comprise a marker ball 701 with an internal threaded hole and a marker pin shaft 702 (refer to FIG. 7) in threaded connection with the marker ball 701. The marker pin shaft 702 is inserted into the connecting hole to realize a fixed connection. The marker ball 701 is made of a metal material, and the marker pin shaft 702 is made of a plastic material.

With reference to FIG. 13, the spherical hinge 1301, the driving joint 1302 and universal hinge 1304 of each strut of the external fixator provide six DoFs for the fixator in total, including that the spherical hinge 301 has three DoFs including rotation R1, R2 and R3 around three axes A1, A2 and A3 which are orthogonal to each other and intersect at one point; the driving joint 1302 has a DoF of translation P1 along axis A3 when a rotating operation 1310 is performed; the universal hinge 304 has two DoFs of rotation R4 and R5 around axes B1 and B2 which are orthogonal to each other.

The above description of the present invention is only exemplary rather than restrictive. Therefore, the embodiments of the present invention are not limited to the specific embodiments described above. If inspired by the present invention, one skilled in the art may make other changes or variations without departing from the spirit of the present invention and the scope protected by the claims, which, however, shall all fall into the protection scope of the present invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A parallel external fixator for fracture reduction for realizing a fracture reduction method, comprising a proximal fixation ring and a distal fixation ring provided below the proximal fixation ring, the proximal fixation ring and the distal fixation ring having the same ring structure, six protrusions being uniformly provided at an interval on a sidewall of the ring structure, a plurality of inner ring connecting holes with an axis in a vertical direction being uniformly provided at an interval in the entire ring structure, and outer ring connecting holes with the axis in the vertical direction being uniformly provided at an interval in the six protrusions, six struts with the same structure being provided between the proximal fixation ring and the distal fixation ring, the six struts being freely configured according to the following rules that: the first strut to the sixth strut are sequentially provided around the circumferential direction of the fixation ring, and every two adjacent struts are not in parallel with each other and do not intersect with each other, wherein:

each strut comprises a spherical hinge, a driving joint, a quick-mounting component and a universal hinge which are sequentially connected from top to bottom; the driving joint is a screw mechanism, a lower section of the screw rod sequentially inserts into a middle threaded hole of a driving nut and a middle hole of a sliding sleeve, the screw rod and the driving nut form a screw pair; the driving nut comprises a cylindrical part, a boss with a diameter smaller than that of the cylindrical part is provided on a top wall of the cylindrical part, an upper part of the sliding sleeve is inserted in the cylindrical part and is in rotary fit with the inner wall of a cavity of the cylindrical part, a plurality of steel ball holes with the axis in the vertical direction are uniformly provided at an interval in the circumferential direction on a top wall of the cavity of the cylindrical part, a spring hole corresponding to a steel ball hole is provided in the top surface of the sliding sleeve, a spring is mounted in the spring hole, the bottom end of the spring is connected with the bottom wall of the spring hole and a steel ball is fixed at the top end of the spring, the depth of the steel ball hole is smaller than the radius of the steel ball, and when the driving nut is rotating, the steel ball is periodically and partially embedded into or withdrawn from the steel ball hole under the effect of the spring to provide a vibration tactile feedback of the amount of rotary movement; an external thread is provided on the outer wall of the sliding sleeve located at the bottom of the cylindrical part, a locking ring sleeves the cylindrical part of the driving nut, and the lower end of the locking ring and the external thread on the sliding sleeve form a threaded connection; a groove is provided in the inner wall of a cavity at the upper end of the locking ring and is embedded with a gasket, the gasket sleeves the boss of the driving nut and is in sliding contact with the top wall of the cylindrical part to limit the axial movement of the driving nut, the locking ring is capable of pressing the gasket or loosening the gasket by rotating the locking ring, and makes the driving joint locked or adjustable; an observation slot is provided along the axial direction of a sidewall of the sliding sleeve, and a telescoping scale mark is provided along the axial direction of the sliding sleeve on the sidewall alongside the observation slot; an axial scale mark is provided along the axial direction of the sliding sleeve at the top end of the observation slot, the lower section of the screw rod is provided with a pin shaft, and the pin shaft is inserted into the observation slot and is capable of sliding relative to the observation slot; the head face of the pin shaft is provided with a transverse scale mark, the transverse scale mark and the telescoping scale mark are provided matching each other to indicate the elongation or shortening value of the strut length; a circumferential scale mark is provided on the outer wall of the boss of the driving nut, the circumferential scale mark and the axial scale mark are provided matching each other to indicate the rotation value of the driving nut relative to the sliding sleeve;

a lower part of the sliding sleeve is connected with an upper part of a removable rod through the quick-mounting component, the upper part of the removable rod has a circle mark, a lower part of the removable rod is provided with an external thread, the external thread of the removable rod and a threaded hole in an upper part of a universal hinge form a threaded connection, and a threaded shaft at a lower part of the universal hinge inserts into an outer ring connecting hole or an inner ring connecting hole in the distal fixation ring and is fixedly connected with the distal fixation ring through a nut;

a first marker, a second marker and a third marker are respectively connected into three connecting holes which are not connected with any parts and are distantly separate from each other in the proximal fixation ring, and a fourth marker, a fifth marker and a sixth marker are respectively connected into the three connecting holes which are not used and are distantly separate from each other in the distal fixation ring; the six markers have the same structure, which respectively comprise a marker ball with an internal threaded hole and a marker pin shaft in threaded connection with the marker ball, the marker pin shaft is inserted into and fixedly connected with the connecting hole, the marker ball is made of a metal material, and the marker pin shaft is made of a plastic material;

wherein the spherical hinge comprises a connecting shaft whose upper end is a threaded shaft, and the threaded shaft of the connecting shaft is capable of inserting into an outer ring connecting hole or an inner ring connecting hole in the proximal fixation ring and is fixedly connected with the proximal fixation ring through a nut; and the lower end of the connecting shaft is pivotally connected with both ends of a long shaft of a cross-shaft component, the cross-shaft component is mounted at an upper part of a revolute connecting sleeve, the outer ends of two short shafts of the cross-shaft component are respectively and pivotally connected into the hole of the revolute connecting sleeve, a plain bearing is pivotally mounted in a cavity of a lower part of the revolute connecting sleeve, an inner ring of the plain bearing is in fixed connection with an upper section of a screw rod, where the upper section of the screw rod inserts into the plain bearing and is fixedly connected with an anti-loosening nut to prevent a threaded connection between the plain bearing and the screw rod from loosening; a back nut is connected with an internal thread at the bottom of the cavity of the revolute connecting sleeve through an external thread, an inner hole of the back nut and the outer surface of the screw rod have a certain clearance, enabling the screw rod and the back nut a relatively free rotation, and the back nut is capable of axially positioning the plain bearing.

2. The parallel external fixator for fracture reduction according to claim 1, wherein the quick-mounting component comprises a locking sleeve with an inner hole, the upper end of the inner hole of the locking sleeve has an internal thread and the lower end is a conical hole; the lower part of the sliding sleeve has an external thread and a conical end, a plurality of notches are provided on the sidewall of the conical end at an interval along a generatrix direction, to form an elastic locking jaw; the sliding sleeve is in threaded fit with the internal thread of the locking sleeve through the external thread, the locking jaw of the sliding sleeve is in conical surface fit with the conical hole of the locking sleeve, and a smooth rod section at a head end of the removable rod passes through the inner hole of the locking sleeve and is inserted into an inner hole of the locking jaw; by using the threaded fit between the sliding sleeve and the locking sleeve and the conical surface fit between the locking jaw and the conical hole of the locking sleeve, a quick switch between fixed connection and detachment of the removable rod and the sliding sleeve can be achieved.

3. The parallel external fixator for fracture reduction according to claim 2, wherein a positioning boss surface is provided between the external threaded rod section and the smooth rod section of the removable rod.

4. The parallel external fixator for fracture reduction according to claim 3, wherein upper and lower edges of the proximal fixation ring and the distal fixation rings are subjected to filleting treatment.

\* \* \* \* \*